(12) United States Patent
Lindvall

(10) Patent No.: US 8,668,692 B1
(45) Date of Patent: Mar. 11, 2014

(54) INTRAMEDULLARY LINKAGE DEVICE, SYSTEM, AND METHOD FOR IMPLANTATION

(71) Applicant: Eric M. Lindvall, Clovis, CA (US)

(72) Inventor: Eric M. Lindvall, Clovis, CA (US)

(*) Notice: Subject to any disclaimer, the term of this patent is extended or adjusted under 35 U.S.C. 154(b) by 0 days.

(21) Appl. No.: 13/753,996

(22) Filed: Jan. 30, 2013

Related U.S. Application Data

(60) Provisional application No. 61/641,138, filed on May 1, 2012.

(51) Int. Cl.
*A61B 17/72* (2006.01)

(52) U.S. Cl.
USPC .................................. 606/62; 623/22.42

(58) Field of Classification Search
USPC .................. 606/62–68; 623/22.11–22.12, 623/22.4–22.46, 23.15–23.38
See application file for complete search history.

(56) References Cited

U.S. PATENT DOCUMENTS

| | | | | |
|---|---|---|---|---|
| 4,878,917 A * | 11/1989 | Kranz et al. | ............... | 623/23.45 |
| 5,032,130 A * | 7/1991 | Schelhas et al. | ............ | 623/22.42 |
| 5,074,882 A | 12/1991 | Grammont et al. | | |
| 5,112,333 A * | 5/1992 | Fixel | ............................... | 606/62 |
| 5,122,141 A | 6/1992 | Simpson et al. | | |
| 5,458,654 A | 10/1995 | Tepic | | |
| 5,489,284 A * | 2/1996 | James et al. | ..................... | 606/62 |
| 5,507,817 A * | 4/1996 | Craig et al. | ................. | 623/20.11 |
| 5,569,249 A * | 10/1996 | James et al. | ..................... | 606/62 |
| 5,626,580 A * | 5/1997 | Brosnahan | ...................... | 606/63 |
| 5,713,901 A | 2/1998 | Tock | | |
| 5,855,579 A * | 1/1999 | James et al. | ..................... | 606/62 |
| 6,264,699 B1 * | 7/2001 | Noiles et al. | ................ | 623/23.23 |
| 6,299,648 B1 * | 10/2001 | Doubler et al. | ............ | 623/23.18 |
| 6,866,683 B2 * | 3/2005 | Gerbec et al. | ............. | 623/18.11 |
| 7,070,622 B1 * | 7/2006 | Brown et al. | ............. | 623/20.14 |
| 7,481,841 B2 * | 1/2009 | Hazebrouck et al. | ...... | 623/18.12 |
| 7,507,256 B2 * | 3/2009 | Heck et al. | ................. | 623/20.15 |
| 7,722,678 B2 | 5/2010 | Brown et al. | | |
| 7,867,282 B2 * | 1/2011 | Heck et al. | ................. | 623/23.46 |
| 7,998,217 B1 * | 8/2011 | Brown | ....................... | 623/20.15 |
| 7,998,218 B1 * | 8/2011 | Brown | ....................... | 623/20.35 |
| 8,100,910 B2 | 1/2012 | Warburton | | |
| 8,303,668 B2 * | 11/2012 | Despres et al. | ............ | 623/22.42 |
| 2002/0007220 A1 * | 1/2002 | Gie et al. | ................... | 623/23.15 |
| 2005/0043811 A1 * | 2/2005 | Doubler et al. | ............ | 623/22.42 |
| 2005/0240275 A1 | 10/2005 | Chappuis | | |
| 2006/0167555 A1 * | 7/2006 | Heck et al. | ................. | 623/20.35 |
| 2007/0005146 A1 * | 1/2007 | Heyligers et al. | .......... | 623/23.46 |
| 2007/0038306 A1 | 2/2007 | O'Gara | | |
| 2008/0262498 A1 | 10/2008 | Fernandez Dell'Oca | | |
| 2010/0094292 A1 | 4/2010 | Parrott | | |

FOREIGN PATENT DOCUMENTS

| | | |
|---|---|---|
| DE | 4129724 | 9/1993 |
| DE | 102008062226 | 8/2009 |

\* cited by examiner

*Primary Examiner* — Mary Hoffman

(74) *Attorney, Agent, or Firm* — Knobbe Martens Olson & Bear LLP

(57) ABSTRACT

The invention relates to an intramedullary linkage device for treatment of peri-prosthetic long bone fractures, system for long bone fracture treatment in the setting of pre-existing intramedullary implant using an intramedullary linkage device and intramedullary fracture fixation device, and methods of treating peri-prosthetic long bone fracture in the setting of pre-existing intramedullary implant using an intramedullary linkage device and intramedullary fracture fixation device.

18 Claims, 20 Drawing Sheets

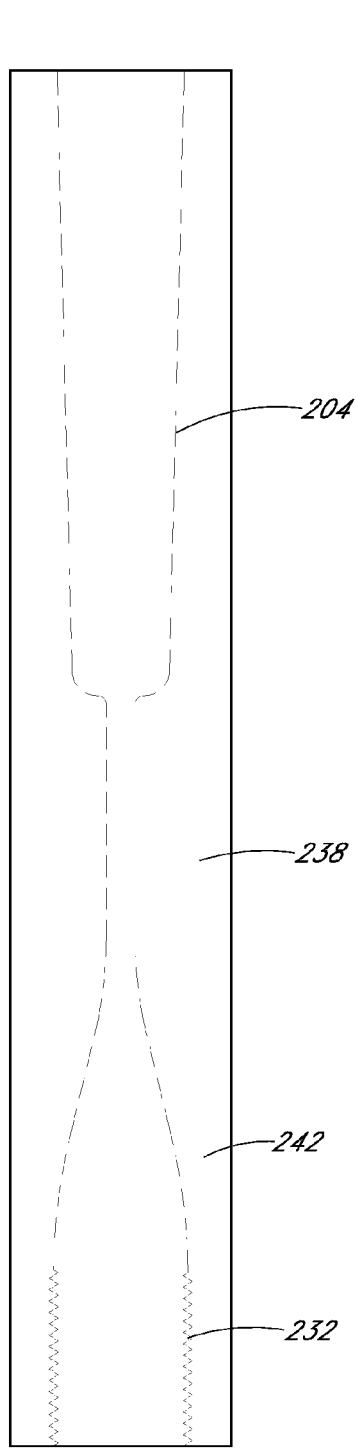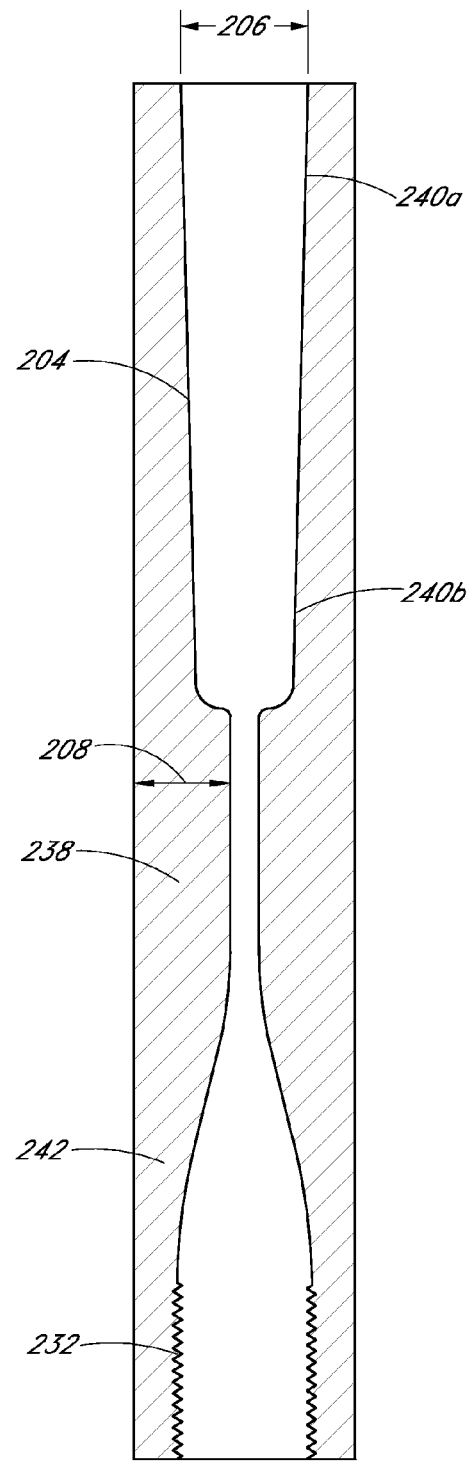
FIG. 5A                    FIG. 5B

INTRAMEDULLARY LINKAGE DEVICE, SYSTEM, AND METHOD FOR IMPLANTATION

CROSS-REFERENCE TO RELATED APPLICATIONS

The present application claims priority under 35 U.S.C. §119(e) to U.S. Provisional Application No. 61/641,138 filed on May 1, 2012, the disclosure of which is incorporated by reference herein in its entirety.

BACKGROUND

1. Field

Disclosed herein is an intramedullary linkage device for use in long-bone fracture fixation, and more particularly, an intramedullary linkage device used for long-bone fracture fixation in the setting of a preexisting implant.

2. Description of the Related Art

Total hip arthroplasty and/or intramedullary hip nail fixation are established treatments for hip arthritis and/or a proximal femur fracture, respectively. With an aging population, these procedures are becoming more and more common. However, with the increased number of hip procedures performed and implants placed comes an increasing number of peri-prosthetic, shaft, or distal femur fractures occurring in patients with preexisting hip implants.

There exist multiple surgical options for this problem, none of which provides a satisfactory solution. Options include removal of the hip implant or prosthesis and replacement with a long-stemmed version, plating of the fracture, often with cable fixation in areas where the preexisting implant blocks screw placement, retrograde intramedullary nail placement from the knee, or a combination thereof. Unfortunately, none of these solutions is an optimal one.

SUMMARY

Therefore, there exists a need for a solution to the problem of long-bone fracture fixation in the setting of a preexisting implant. Disclosed herein is a novel design for an intramedullary linkage device to be used in the setting of a preexisting implant in a long-bone fracture, a system for a fracture fixation with a preexisting intramedullary implant, and methods for use of an intramedullary linkage device to treat a long bone fracture.

There remains a need for treatment of these difficult peri-prosthetic long-bone fractures that permits retention of a functioning and stable preexisting implant, while optimizing fixation of the immediate fracture and avoiding stress risers in the shaft. There is also a need for a system which provides a manageable number of implants that are capable of fixing the vast majority of peri-prosthetic fractures.

These and other needs are addressed by an intramedullary linkage device, peri-prosthetic fracture system, and related methods for use disclosed herein. Specifically, there is provided an intramedullary linkage device comprising a generally cylindrical shape with a proximal opening into a channel configured to mate universally with preexisting intramedullary implants, and a distal opening configured to accept an intramedullary fixation implant. Methods for implantation include preparation of the intramedullary canal, impaction of the linkage device over the tip of the preexisting intramedullary implant, and coupling of the linkage device to an intramedullary fracture fixation nail. Systems of different sizes of linkage implant and intramedullary nails are provided to fit the vast majority of patients. These are designed to interchangeably couple with one another. Ancillary equipment, such as locking screws, inserters, extractors, plugs, and other hardware may also be provided with the system. Linkage devices may also be provided with universal coupling channels on both the proximal and distal end, to accommodate any intramedullary nail choice by the surgeon, as well as preexisting implants of various shapes and sizes. Custom nails may also be manufactured to address unusual situations. Systems and linkage devices may also be provided for the treatment of femoral shaft or proximal femur fracture in the setting of a distal implant or prosthesis or in the treatment of other long bone fractures with preexisting implants; for example, in the tibia, radius, ulna, humerus, hand or foot.

One embodiment of the invention comprises a linkage device for use in the intramedullary canal of a long bone, the device comprising an elongate, rigid body having a first end wherein the surface of the first end is configured for cutting bone and a second end, a substantially smooth outer surface, and a lumen extending through the elongate body from the first end to the second end, wherein the lumen includes a first section adjacent the first end, having an inner diameter sized to mate with an intramedullary portion of a first bone implant, wherein the diameter of the first section tapers from the first end toward the second end, a second section adjacent the second end, having an inner diameter sized to mate with an intramedullary portion of a second bone implant wherein at least a portion of the second section is internally threaded, and a central section disposed between the first and second sections and having an inner diameter smaller than either the first section inner diameter or the second section inner diameter.

In another embodiment of the linkage device, the first end of the elongate, rigid body is beveled.

In another embodiment of the invention, the first section of the lumen of the linkage device is tapered such that an angle between an outer wall of the first section and the inner wall of the first section is between 0.5 and 10 degrees. In an embodiment of the linkage device, the angle between the outer wall and inner wall of the first section is constant. In another embodiment of the linkage device, the angle between the outer wall and inner wall of the first section increases from the first end of the linkage device toward the second end.

In an embodiment, the linkage device further comprises a plug in the distal portion of the first section of the linkage device which extends into the lumen of the central section of the linkage device.

In an embodiment of the linkage device, the lumen of the second section comprises a tapered portion adjacent the second end of the linkage device and a threaded portion adjacent the central portion of the linkage device. In an embodiment, the threaded portion is configured to mate with an inserter tool. In another embodiment, the tapered portion is configured to mate with the intramedullary portion of the second implant.

In an embodiment, the first section of the linkage device is between 3 and 6 cm. in length, the second section is between 3 and 6 cm in length and the central section is between 1 and 4 cm in length. In an embodiment, the external diameter of the linkage device is between 9 and 16 mm.

A method for peri-prosthetic long bone fracture fixation comprises preparing an intramedullary canal of a fractured long bone with a preexisting prosthesis stem, inserting an intramedullary linkage device into the intramedullary canal wherein the intramedullary linkage device comprises an elongate body with a first end and a second end with a lumen extending through the elongate body from the first end to the second end wherein the lumen comprises a first section adjacent the first end wherein a wall of the lumen describes a taper wherein a widest diameter of the lumen in the first section is adjacent the first end, and a second section adjacent the second end wherein the lumen is configured to accommodate an intramedullary fracture fixation device, obtaining a friction fit between the first section of the intramedullary linkage device and the preexisting prosthesis stem, inserting an intramedullary fracture fixation device into the intramedullary canal, and coupling the intramedullary fracture fixation device to the second section of the intramedullary linkage device.

In one method for peri-prosthetic long bone fracture fixation, coupling the intramedullary fracture fixation device to the second section of the intramedullary linkage device comprises obtaining a friction fit between the second section of the intramedullary linkage device and the intramedullary fracture fixation device.

A method for peri-prosthetic long bone fracture fixation further comprises coupling an inserter tool to the second section of the intramedullary linkage device prior to inserting the intramedullary linkage device in the intramedullary canal.

A system for peri-prosthetic long bone fracture fixation comprises an at least one intramedullary linkage device comprising an elongate body with a first end and a second end with a lumen extending through the elongate body from the first end to the second end wherein the lumen comprises a first section adjacent the first end wherein a wall of the lumen describes a taper wherein a widest diameter of the lumen in the first section is adjacent the first end, and a second section adjacent the second end wherein the lumen is configured to accommodate an intramedullary fracture fixation device and an at least one intramedullary fracture fixation device comprising a leading end and a trailing end wherein the leading end is configured to couple with the intramedullary linkage device.

A system for peri-prosthetic long bone fracture fixation further comprises an inserter tool. A system for peri-prosthetic long bone fracture fixation further comprises a trephine. A system for peri-prosthetic long bone fracture fixation comprises two or more intramedullary linkage devices in which an external diameter of one intramedullary linkage device is smaller than an external diameter of the second intramedullary linkage device.

BRIEF DESCRIPTION OF THE DRAWINGS

FIG. 5A shows an anterior view of a femoral linkage implant;

FIG. 5B is a longitudinal cross-sectional view of the same linkage implant, with axial cross-sections;

DETAILED DESCRIPTION

Anatomy

Figure 1:
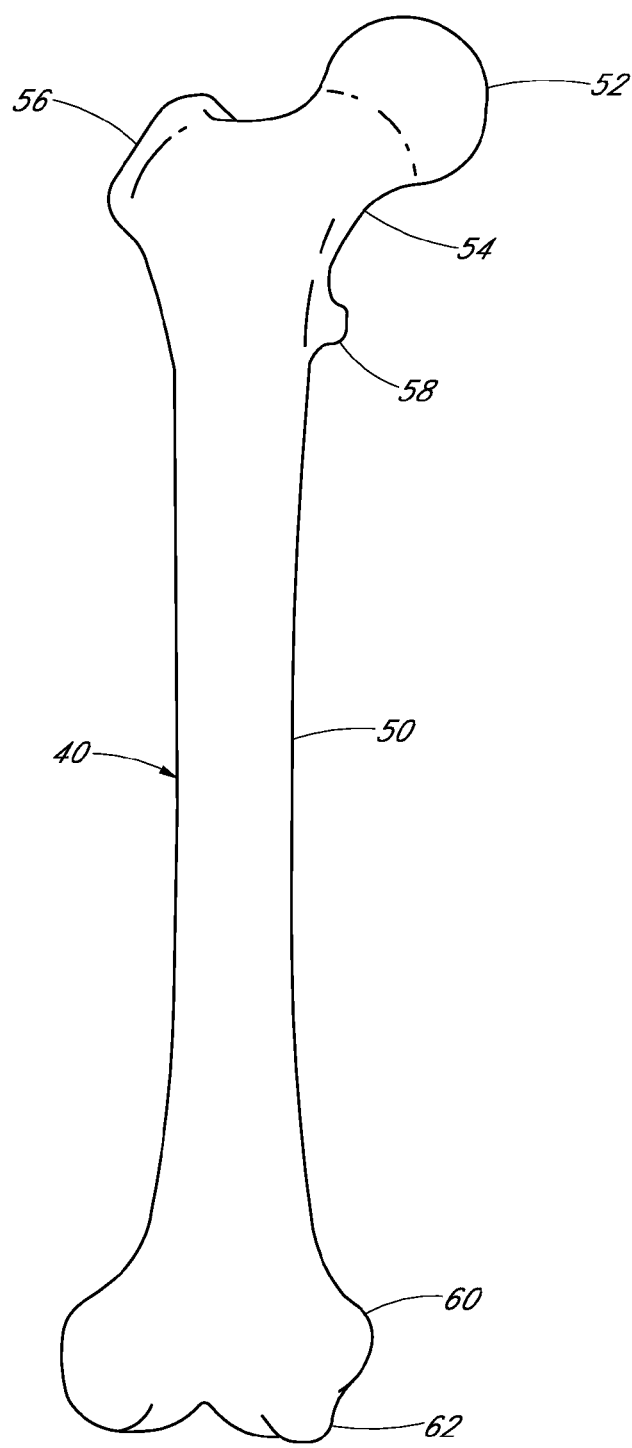
FIG. 1 is an anterior view of a human femur.

FIG. 1 illustrates aspects of the human femur 40. The shaft of the femur 50 connects proximally with the neck 54 and head 52. The greater trochanter 56 and the lesser trochanter 58 are illustrated at junction of the neck 54 and shaft 50 sections of the femur bone. Distally, the femoral shaft 50 widens into the metaphyseal 60 region. Distal to the metaphysis is the articular surface 62 at the knee.

Figure 2A:
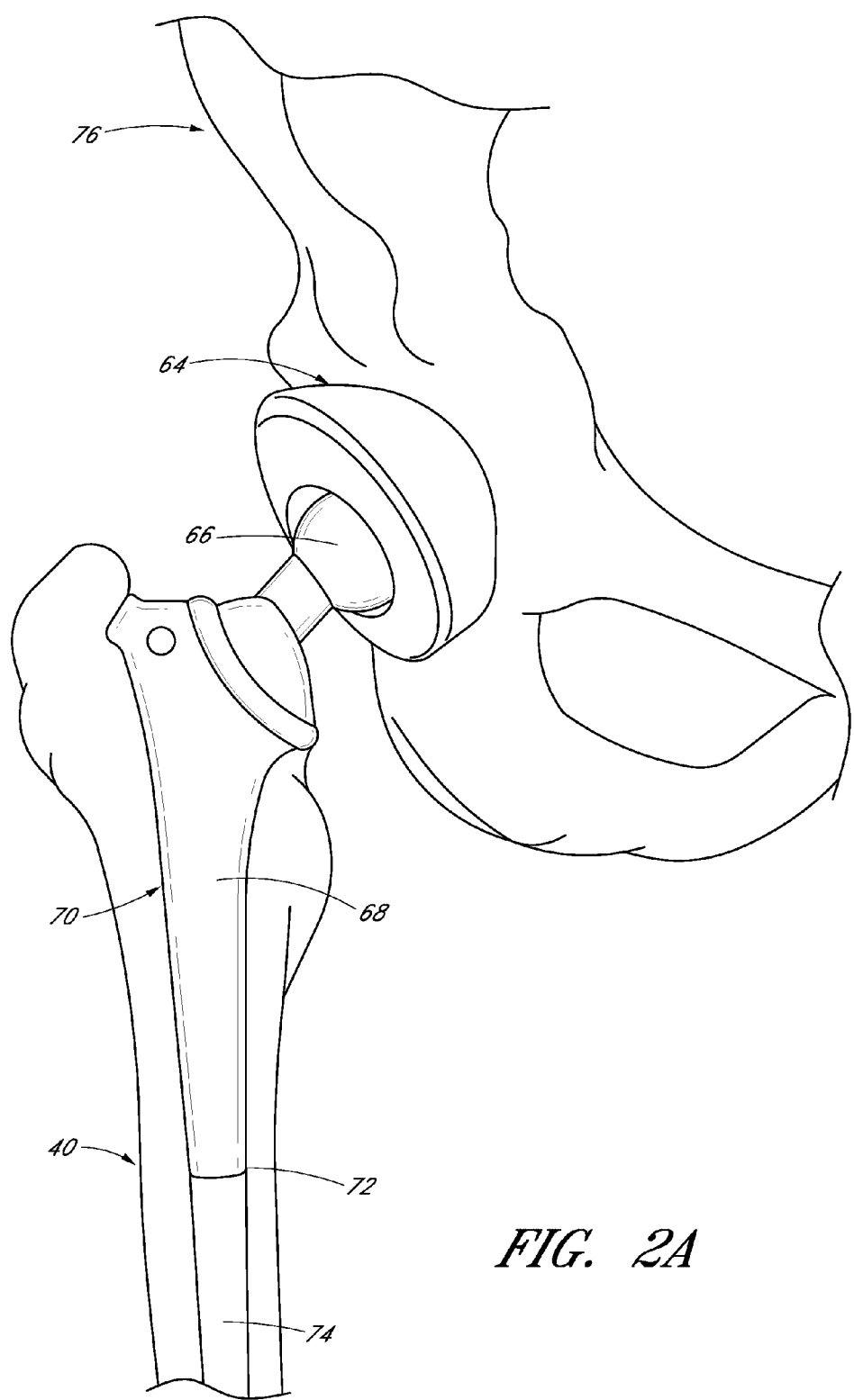
FIG. 2A is an anterior view of a hip replacement prosthesis.
Figure 2B:
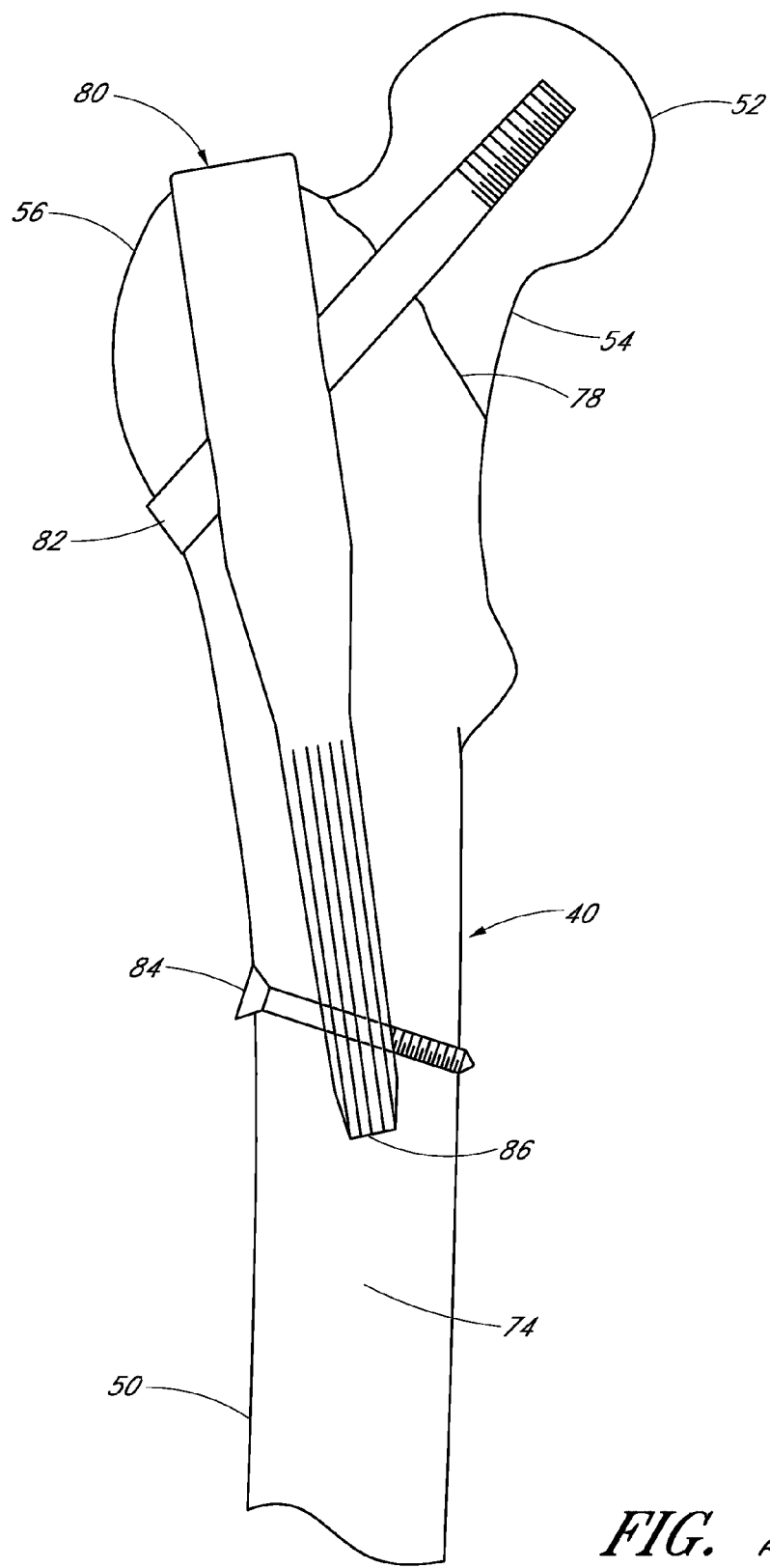
FIG. 2B is an anterior view of a proximal femur with a fracture and a short intramedullary hip nail.

It is increasingly common, in the setting of a femoral neck fracture or advanced hip arthritis, for patients to undergo partial or total hip arthroplasty. FIG. 2A illustrates a typical hip replacement with acetabular component 64 set within the pelvis 76 and femoral stem 68 of the femoral prosthesis coupled to femoral head component 66. The distal tip 72 of the femoral prosthesis 70 can be seen terminating within the intramedullary canal 74. Alternatively, many older patients may sustain a proximal femoral fracture 78, such as the intertrochanteric fracture shown in FIG. 2B. This may be treated with an intramedullary hip nail 80, which is often placed through the greater trochanter 56 into the intramedullary canal 74 of the femur 40. One or more cannulated hip screws 82 may pass through the intramedullary hip nail 80, crossing the fracture site 78 and terminating in the femoral head 52. Rotation may be fixed with a locking screw 84 distally. The distal tip 86 of the nail terminates in the upper portion of the femoral shaft 50.

Figure 2C:
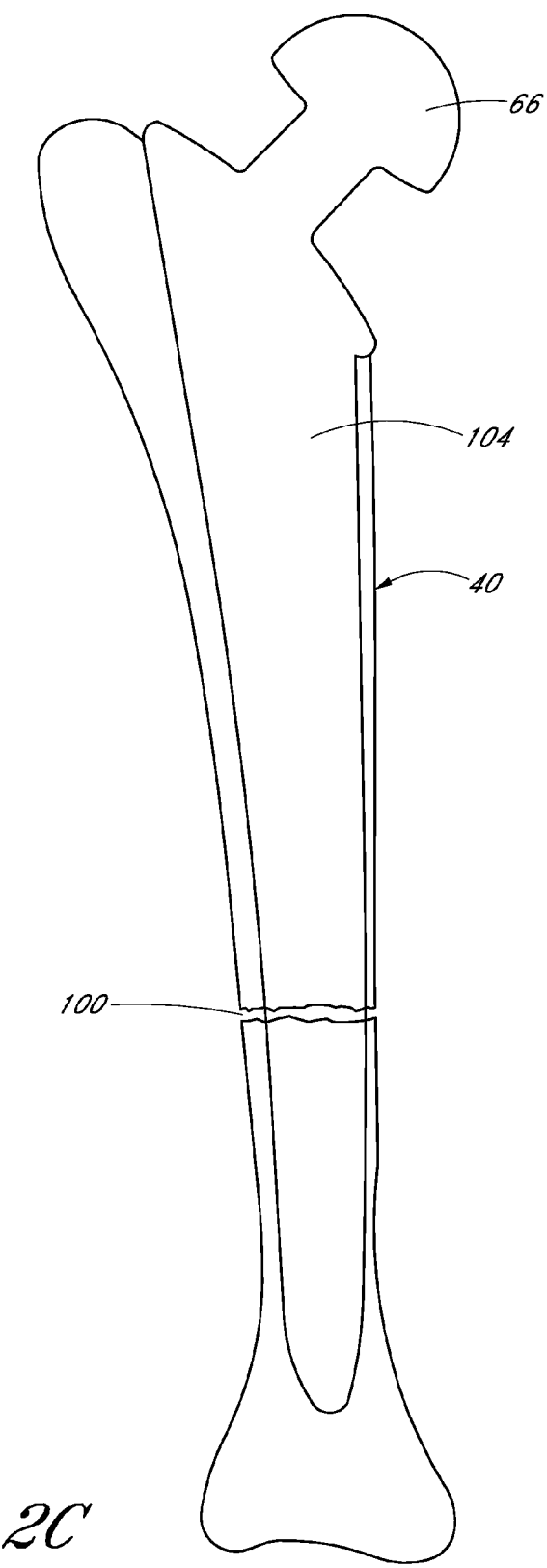
FIG. 2C is an anterior view of a femur with exemplary long-stemmed prosthesis.

Turning to FIG. 2C, one solution for a peri-prosthetic femur fracture 100 is illustrated. The first prosthesis has been removed and a new, long-stem or custom, prosthesis 104 has been substituted. The long stemmed prosthesis may or may not include cross-screws distally (not shown). Revision of the original implant is an unsatisfactory solution. First, a functional and stable implant may have to be removed. This revision exposes the patient to all of the attendant morbidities and mortalities involved in a revision hip replacement surgery, including, but not limited to, further fracturing of the femur 40, either during removal of the original implant or during impaction of the new implant, loosening of the new implant, dislocation of the new implant, infection, wound issues, nerve damage, morbidity from extensive dissection, and bleeding. In addition to problems caused with the hip replacement, this may provide sub-optimal fracture fixation. Furthermore, it can be very technically difficult to place the prosthesis 104 in the setting of a fresh, unstable fracture; for example, during impaction of the implant, the fracture site may separate, which may increase the likelihood of a fracture non-union or malunion. As is well-known by those skilled in the art, hip revision prostheses generally have a shorter functional lifespan than an original, or primary, prosthesis, and each subsequent revision surgery exacerbates this problem. It is, therefore, strongly preferred to retain an original prosthesis in the setting of a peri-prosthetic fracture when it is possible to do so.

Figure 3:
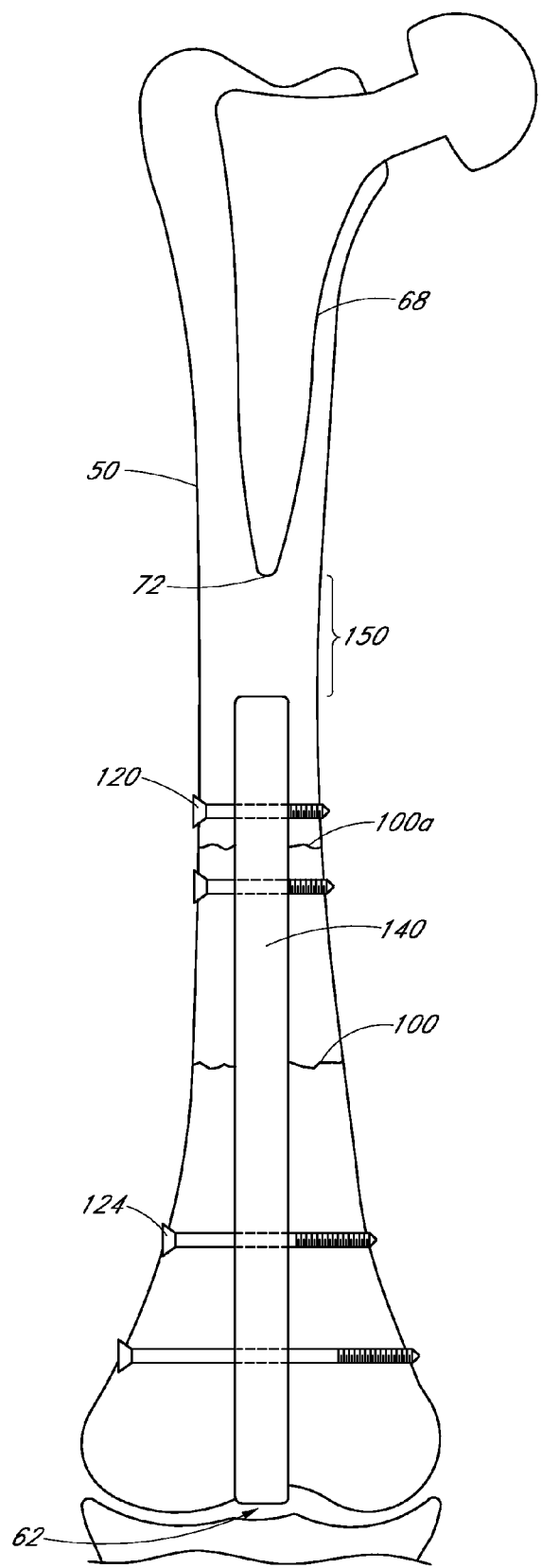
FIG. 3 is an anterior surface view of a femur with hip prosthesis and retrograde distal femoral nail.

Illustrated in FIG. 3 is another currently employed solution for a distal femur or femoral shaft fracture 100 in the setting of a preexisting prosthesis 68. An exemplary retrograde femoral nail 140 can be seen extending from the knee 62. Locking screws may be placed distal 124 and proximal 120 to the fracture 100 to provide rotational control and prevent longitudinal motion at the fracture site. However, this construct has several disadvantages. First, if the fracture is, instead, relatively proximal 100*a* on the shaft 50, a retrograde nail 140, which cannot extend beyond the tip of the prosthesis 72, may only extend a short distance on the proximal side of the fracture 100*a*. Therefore, an unfavorable lever arm may be present, and excessive motion at the fracture site 100*a* may occur. This risks loosening of the nail implant 140, fracture at the tip of the nail 140, or non-union of the fracture 100*a*. Even if adequate fixation may be obtained both proximally and distally to the fracture site, there is at least a short zone 150 between the two implants where only the native bone is present. The patient population with a hip implant, whether for the treatment of arthritis or a proximal femoral fracture is generally predisposed to have weak bone due to age, disuse, or other factors. This is particularly true of those who sustain a second femoral fracture, which has often occurred with little trauma. The unsupported segment 150 of native femur between the tip of the stem proximally 72 and the intramedullary nail distally 140 is particularly vulnerable to fracture in comparison to the surrounding bone which has the additional strength of the intramedullary implant. If significant bending or twisting force is applied to the bone, fracture at the unsupported portion of the femur 150 is likely to occur.

Figure 4A:
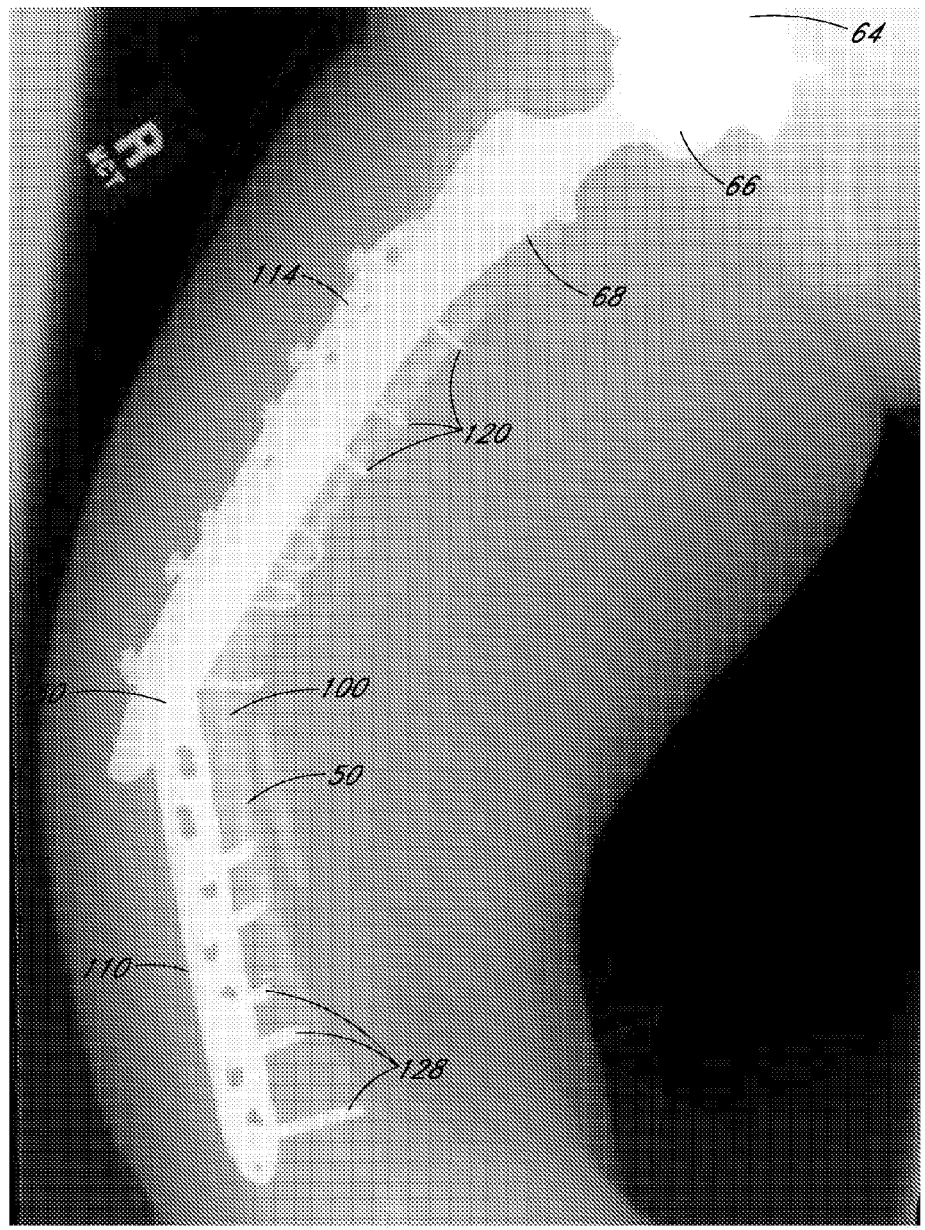
FIG. 4A is a lateral radiograph view of a femur fracture with hip prosthesis and screw and plate fixation, wherein the plate has fractured.
Figure 4B:
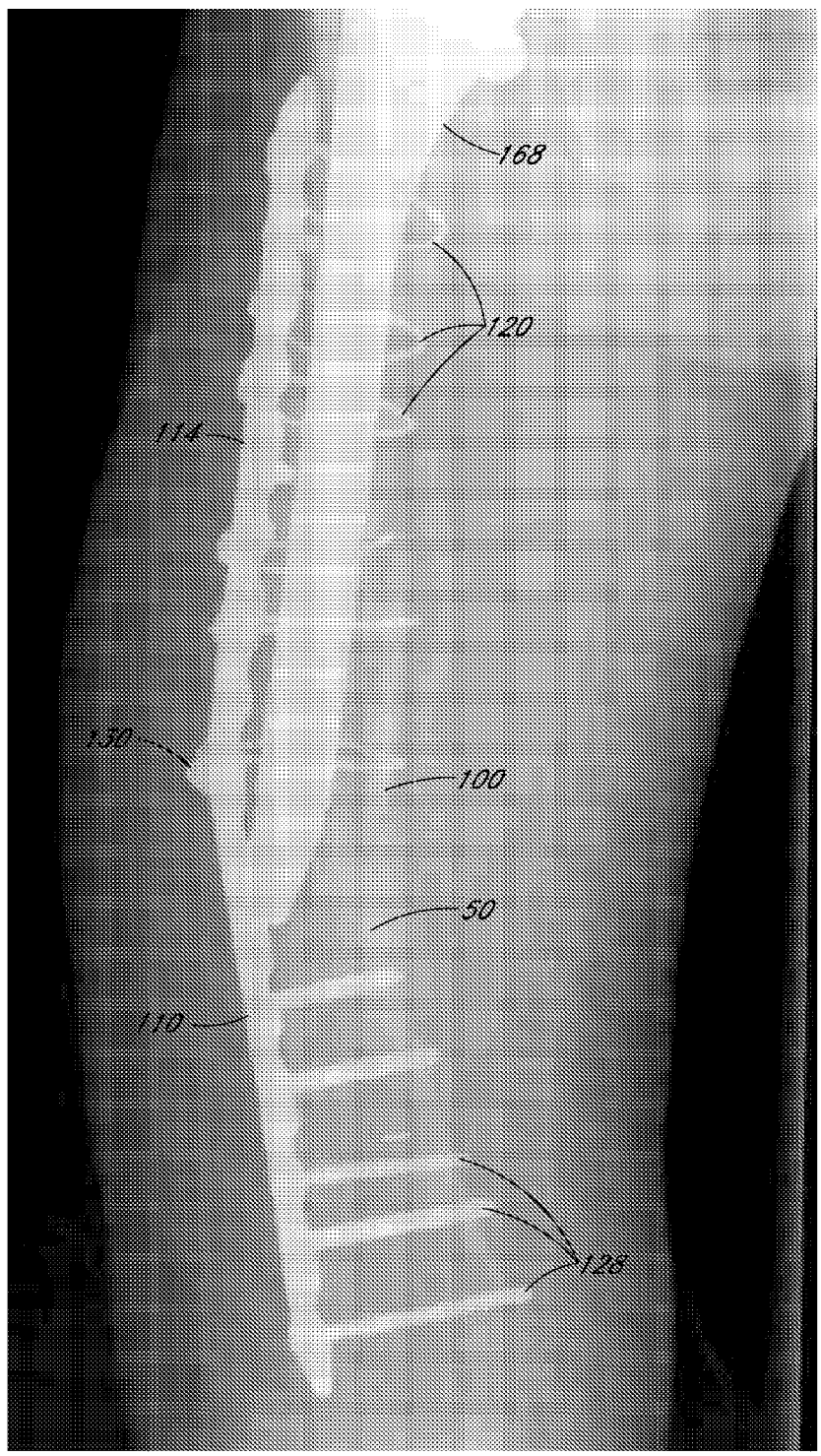
FIG. 4B is an anterior-posterior radiograph view of the femur fracture of FIG. 4A.

Turning to FIGS. 4A and 4B, a third solution for femur fractures in the setting of a preexisting prosthesis is illustrated, as is one of the complications thereof. A prosthesis 68 with acetabular component 64 and femoral head component 66 may be visualized in the proximal femur. A peri-prosthetic fracture 100 of the shaft is seen near the tip of the prosthesis. The fracture has been stabilized using a long lateral side plate 114. The long lateral side plate 114 has been fixed distally with screws 128. Proximally, because the prosthesis 68 blocks placement of transverse screws across the femur, fixation may be accomplished using cables 120. However, as shown in FIGS. 4A and 4B, if the fracture 100 does not heal, the plate may eventually break, as shown at point 130. Other drawbacks of plate treatment of peri-prosthetic fractures include plate loosening, extensive periosteal stripping, large incisions, extensive blood loss, and potential malunions, or as demonstrated, non-unions of the fracture.

Embodiments of the Intramedullary System

Linkage Device

Turning now to FIGS. 5A and B, an anterior view of an embodiment of the intramedullary system can be seen. FIG. 5A shows a substantially cylindrical device with proximal and distal ends and an outer diameter. Noted proximally is an interior diameter defining a lumen or channel. This lumen extends the length of the nail, as may be seen in FIG. 5B, and may be divided into three sections—a first, proximal section 204, a second, middle section 238, and a third, distal section 242. The proximal section 204, as can be seen in FIG. 5A, a longitudinal cross-section of the embodiment, tapers from proximal 204*a* to distal 204*b*, such that the lumen or channel defined in the proximal section has a diameter 206 which decreases from proximal to distal. At the same time, it can be seen that the implant width 208 between the exterior and interior surfaces of the nail increases from proximal to distal in this first section 204. The central section 238 can be seen to have a relatively narrow diameter of the channel or cannulation, with a consequent increase in implant width 208 between the internal and external surfaces. The third, distal section 242 may have a narrowest point at the junction with the second section which generally increases to the distal end of the prosthesis. In this embodiment, a segment of the third section 242 may have an essentially cylindrical channel, which may be threaded 232. Alternatively, this area may have protrusions or indentations in the luminal surface, for accepting corresponding indentations or protrusions of a complementary implant.

Figure 6:
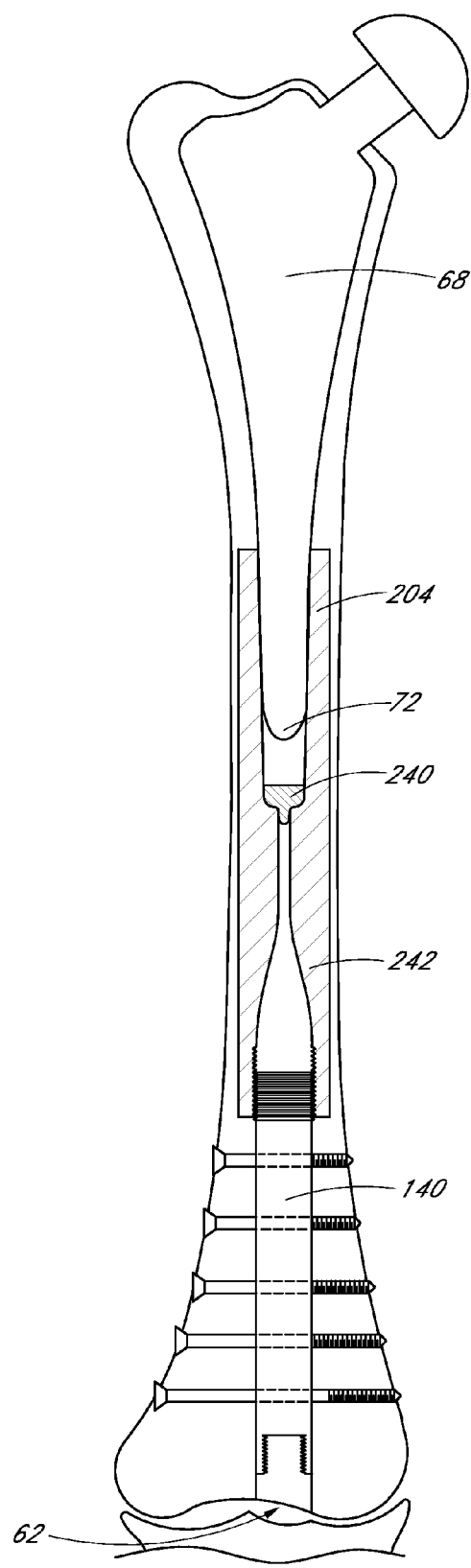
FIG. 6 is an anterior view of a femur, with hip prosthesis, linkage implant, and retrograde intramedullary nail.

Turning to FIG. 6, an embodiment of the linkage device is seen implanted into a femoral bone of a patient. The preexisting prosthesis 68 can be seen proximally with the distal tip of the prosthesis 72 mated to the tapering channel of the first section 204 of the linkage device. Distally, the third section 242 is coupled to a proximal end of a intramedullary device 140, which was inserted at the knee 62. The coupling of the linkage device and the femoral nail occurred by engaging external, male threads of the distal intramedullary rod implant with interior, female threads of the third section 242 of the linkage device channel.

The linkage implant may be manufactured from any of a number of suitable materials. These may include, but are not limited to, such materials as surgical stainless steel, cobalt chromium, titanium, or other biocompatible materials. biocomposite or bioabsorbable materials may also be used.

The dimensions of the intramedullary device include an overall length which may be, in some embodiments, about 15 cm. In other embodiments, the intramedullary linkage device may be in the range of 12 to 18 cm. In yet still other embodiments, the device length may be about 9 cm, 10 cm, 11 cm, 12 cm, 13 cm, 14 cm, 16 cm, 17 cm, 18 cm, 19 cm, or 20 cm.

The device may be provided in a variety of external diameters. For example, the external diameter of the linkage device may be in the range of about 8 mm to about 18 mm. In some embodiments, the external diameter may be in the range of about 10 mm to about 15 mm. In some embodiments, multiple linkage devices with different external diameters may be provided to accommodate a wide variety of intramedullary canals. For example, the device may be provided in a small, medium and large size, although either more or fewer sizes may be provided, such as two, four, or five sizes. The small size may be about 11 mm, the medium size may be about 13 mm, and the large size may be about 15 mm. Other sizes may be 10 mm, 12, mm, 14 mm, or 16 mm. Each size may have an external diameter either smaller or larger than the ranges provided.

The external surface of the intramedullary linkage device may be smooth. This may provide an advantage in later extraction, as bony ingrowth will be inhibited and there will be little interaction between the cortical bone and the external surfaces of the implant. In some embodiments, where it is desired that the implant be placed permanently, the external walls may be roughed, have protrusions and/or indentations to promote bony ingrowth, or have plasma sprayed particles or other similar surface modifications known to one skilled in the art. Similarly, the first and third section channel walls may be smooth or may have surface roughening for enhanced frictional fit.

Proximal Segment

Figure 7A:
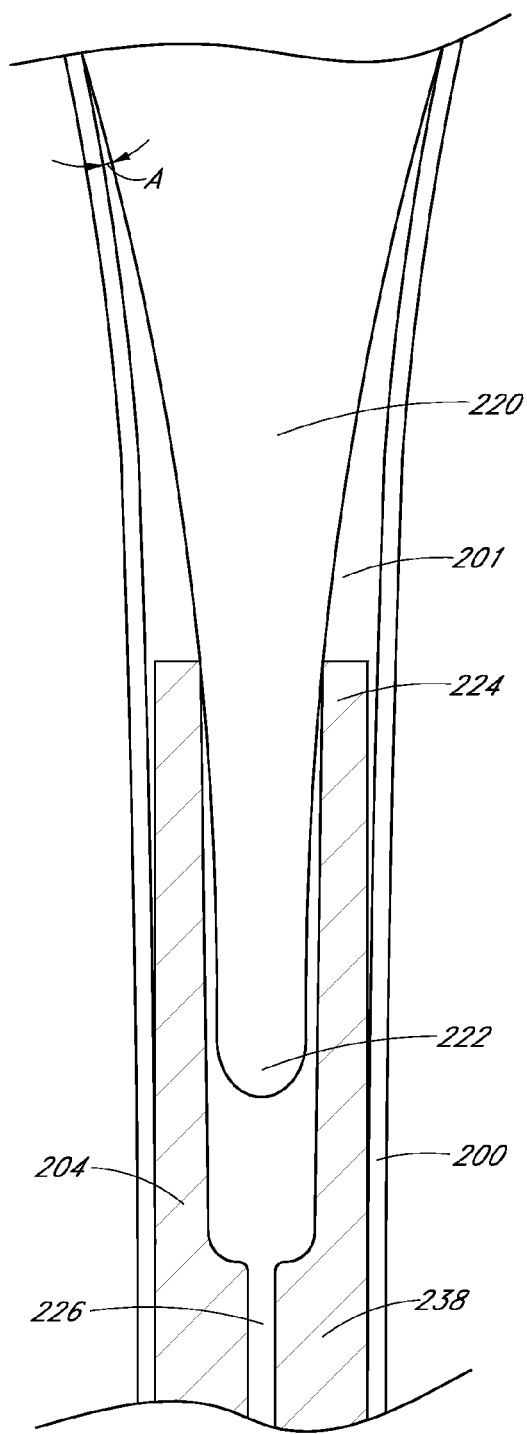
FIG. 7A is a longitudinal cross-sectional view of the proximal portion of a linkage implant in the femur, showing coupling to a tapered prosthesis stem.
Figure 7B:
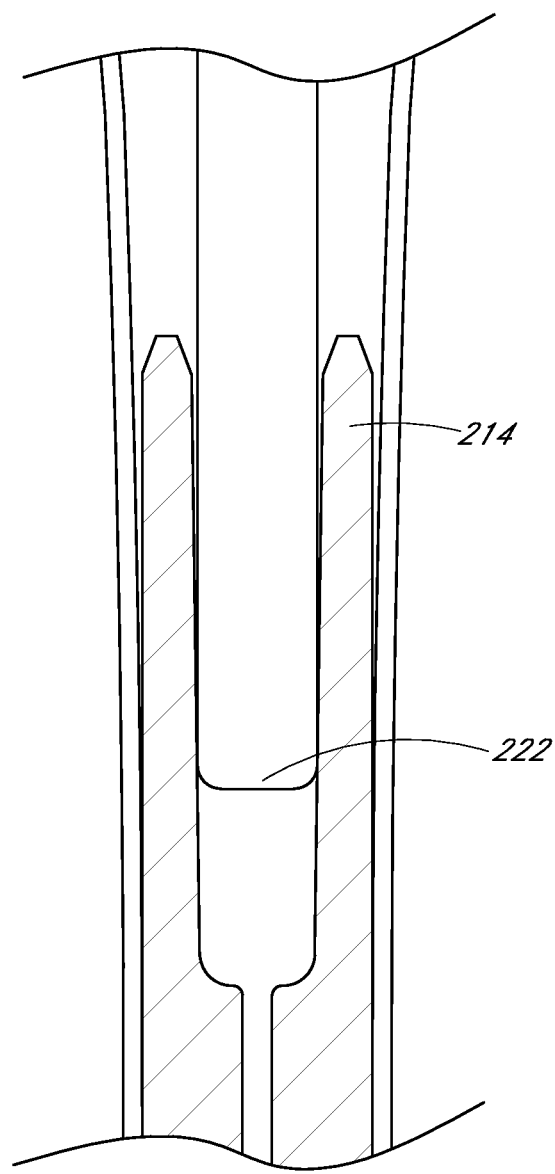
FIG. 7B is a longitudinal cross-sectional view of the proximal portion of a linkage implant in the femur, showing coupling to a generally cylindrical prosthesis stem.

In FIG. 7A, the first, proximal section 204 of a linkage device 210 is illustrated implanted within the intramedullary canal 201 of the femur 200. This first section 204 transitions into a second, middle section 238 of the device with cannulation 226. Prosthesis stem 220 with distal tip 222 is shown; in this embodiment, the femoral prosthesis 220 is tapered towards its end 222. Therefore, a friction fit is obtained between the proximal end 224 of the linkage device and the portion of the prosthesis 220 with a corresponding diameter. In FIG. 7B, a prosthetic implant 220 is shown with a cylindrical rather than a tapered tip 222. In this case, the frictional fit occurs between the end of the implant and the place along the tapered surface of the first section 204 with a corresponding diameter. In some embodiments, as can be seen in FIG. 7B, the leading, proximal edge 214 of the linkage device may be beveled or otherwise shaped to form a cutting edge. This may be of advantage when implanting the prosthesis to aid in the disruption of bony in-growth around the prosthesis tip and improve the frictional fit. A beveled edge may also provide an advantage in guiding the leading edge 214 of the linkage device over the tip 222 of the prosthesis.

The longitudinal dimension of the first, proximal section 204 of the linkage device may be, in one embodiment, about 6 cm from the first, leading edge 224 to its junction with the second section 238. In other embodiments, the length may be about 2 cm, about 3 cm, about 4 cm, about 5 cm, about 7 cm, or about 8 cm.

The widest portion of the channel or lumen of the first section 204 is at the leading or proximal end and the diameter narrows along the length of the proximal section toward its junction with the second section. This taper or narrowing may describe a generally constant angle A between the inner and outer surfaces of the linkage device, or it may vary along the course. For example, in some embodiments, the proximal portion of the interior surface of the linkage device may be relatively parallel to the external surface initially, with increasing curve such that the angle becomes greater toward the distal portion of the wall. In other embodiments, the angle A is relatively constant between the internal and external wall surfaces. For example, the angle A between the interior and the internal and external walls may be in the range of about 0.1° to 0.8°. The angle described in other embodiments may be about 0.25°, 0.5°, 0.75°, 1°, 2°, 3°, 4°, 5°, 6°, 7°, 8°, 9°, 10°, 11°, or 12°.

In some embodiments, the proximal edge 224 may have a width of about 1 mm. In other embodiments, the width may be 0.25 mm, 0.5 mm, 0.75 mm, 1.25 mm, 1.5 mm, 1.75 mm, or 2 mm. The edge may be a blunt, beveled, pointed, rounded, or a combination of contours.

An insert or cap may be provided which may integrated into, removably coupled with, or inserted into the proximal section 204 of the linkage device. This insert may be comprised of an ultra-high molecular weight polyethylene, polyetheretherketone (PEEK), polyetherketoneketone (PEKK), polyethylene, fluoropolymers, elastomers, ceramics, zirconia, alumina, silicon nitride or combinations of these materials. This may be advantageous to use in the setting of a preexisting prosthesis of an unknown material, unusual coating, or one different than those provided in linkage devices. Positioning an insert comprised of a relatively inert material between the metal portion of the linkage device and the distal tip of the prosthesis may avoid metallosis or formation of other debris due to the interaction between two different surfaces. In addition, an insert may be advantageous if the prosthesis tip is of an unusual size or shape, in that it may permit frictional fit by decreasing the channel size. If an insert is provided of compressible material, the insert may increase the contact area between the linkage device and the prosthesis as well.

Figure 8:
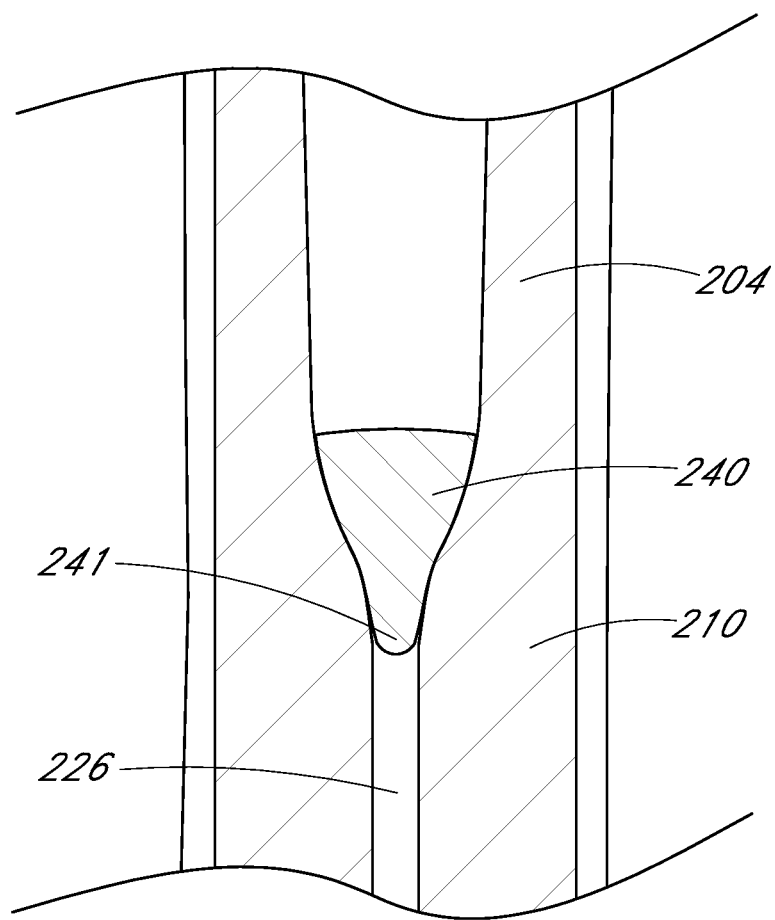
FIG. 8 is a blown-up longitudinal cross-sectional view of a linkage implant at the first, proximal and section, middle junction, showing an optional plug.

Turning now to FIG. 8A, an optional plastic plug 240 may fit into the distal-most portion of the first section 204 of a linkage device, with a narrowed end 241 which extends into the central cannulation 226 of the middle portion 238. This plug may generally funnel-shaped in some embodiments, and in others, may be generally cylindrical with a short protrusion 241 for blocking the linkage device cannulation 226. The plug may be comprised of any of a variety of appropriate materials, including ultra-high molecular weight polyethylene, polyetheretherketone (PEEK), polyetherketoneketone (PEKK), fluoropolymers, elastomers, foam, silicones, combinations of these materials or other suitable materials. The plug may prevent materials from entering into and blocking the central cannulation 226 or distal portion of the linkage device 210. This feature allows a method of implantation in which bone cement such as polymethylmethacrylate (PMMA) may be placed in the distal segment and, upon implantation, fill the space between the prosthesis stem and channel wall of the prosthesis distal to the friction fit. This may supplement fixation of the device to the prosthesis. The plug may be supplied separately for assembly prior to implantation or may be supplied integral to or previously assembled to a linkage device. In addition to preventing PMMA from blocking the cannulation 226, when PMMA is used, later extraction of the device may be facilitated by the inclusion of the plug. The plug 240 may remain in the femoral intramedullary canal, embedded in the distal tip of the PMMA plug, after the implant is extracted. This facilitates extraction because it may require less force to disrupt the PMMA-to-linkage device interface where the internal wall is essentially parallel to the direction of removal, because the shear force required to do so is significantly less than, for example, a force necessary to disrupt the interface when the force is being applied perpendicular to the interface, as would be required at the distal tip of the cement plug. In some embodiments, the plug may be removeably coupled to a guide wire such that it may be placed in the intramedullary canal prior to insertion of the linkage device, the linkage device may be inserted over the guide wire, and the guide wire withdrawn into the device until the plug is seated at the junction of the first and second sections. At that point, the coupling to the guide wire may be undone and the guide wire extracted from the canal. Alternatively, after seating the plug, the guide wire may remain coupled until after the intramedullary fracture fixation device and used to guide it into position past the fracture site. After the intramedullary fracture fixation device is coupled to the linkage device, the guide wire may be uncoupled from the plug and fully withdrawn.

Middle Segment

The second, middle, section 238 of the linkage device comprises a relatively narrow diameter channel or cannulation 226. The diameter of the channel may be about 3.3 mm, corresponding to a standard sized cannulation and standard sized guide wires well-known to those skilled in the art. The central cannulation may also have a diameter of about 1.5 mm, 1.8 mm, 2.0 mm, 2.25 mm, 2.5 mm, 2.75 mm, 3.0 mm, 3.5 mm, 3.75 mm, 4.0 mm, 4.25 mm, or about 4.5 mm in diameter. Cannulation 226 provides a number of advantages. Where fracture reduction is difficult to maintain during implantation, and a plastic plug 240 is not used, the cannulation permits passage of a guide wire past the fracture site to guide implantation of the linkage device past the fracture site. This ensures that the proximal end of the linkage device is passed through the fracture site and into the intramedullary canal of the femoral shaft proximally, rather than outside the femur on the far side of the fracture, which risks injuring soft tissues. Furthermore, the cannulation may help maintain a relatively consistent overall strength along the length of the femur, whereas a solid central portion would be significantly stiffer than other areas, for example, at the proximal edge of the linkage device, where it is relatively thin-walled. This mismatch could create a "weak spot" which might be at risk for fracture, fatigue at the prosthesis-linkage device interface, or other problems.

The middle section 238 of the linkage device may have a total length of about 3 cm in some embodiments. In other embodiments, the length of the middle section may be about 1 cm, about 1.5 cm, about 2 cm, about 2.5 cm, about 3.5 cm, about 4 cm, about 4.5 cm, or about 5 cm. The transitions both between the first 204 and middle 238 sections and the middle 238 and distal 242 sections of the linkage device may be gradual, describing a concave curve. In other embodiments, the transition or transitions may describe essentially a right angle.

In other embodiments, the linkage device may not have a through-channel extending from the proximal edge to the distal edge. Instead, the central portion between the proximal receiving channel and the distal receiving channel may be solid.

Distal Segment

Figure 9:
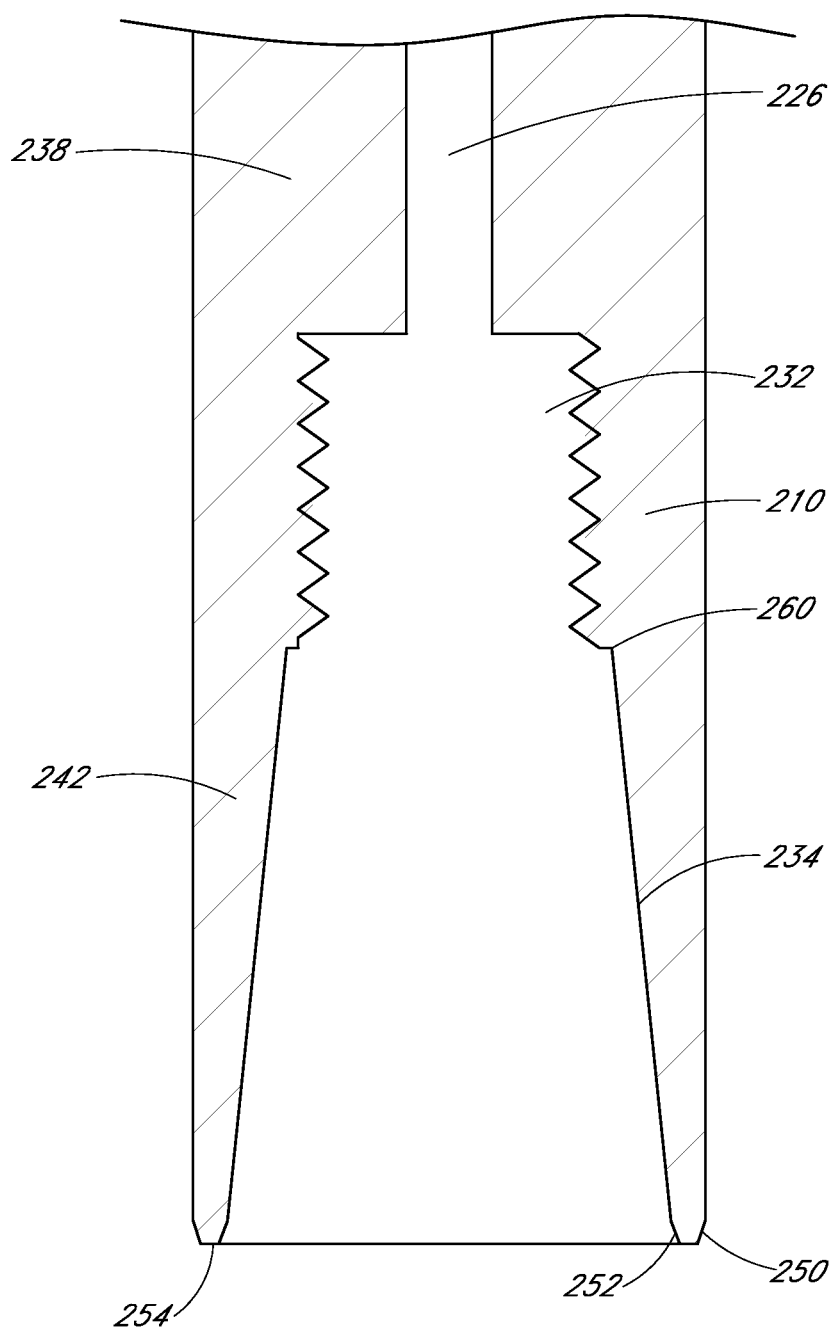
FIG. 9 is a blown-up longitudinal cross-sectional view of the distal, third section of a linkage implant.

FIG. 9 shows an embodiment of the distal, third section 242 of a linkage implant 210. After transition from the middle section 238, the diameter of the central channel widens and continues at a relatively constant diameter for a length until transition 260 where a widening taper continues until the distal edge 254. The proximal portion of the third section comprises an internal thread 232 for removable coupling with an inserter and/or extractor tool. The tapered section 234, which is distal to the threaded section 232, comprises a taper configured to form a friction, interference fit with a corresponding retrograde femoral nail.

In some embodiments, the distal edge 254 comprises inner 252 and outer 250 beveled surfaces. Alternatively, either an inner 252 or an outer 250 beveled surface may be provided. In still other embodiments, the edge is flat and transitions directly into external, exterior and interior walls of the linkage device. In the embodiments with a beveled edge, insertion of the intramedullary nail may be facilitated by guidance from the beveled surface. Should the linkage device later require extraction, beveling also may assist in guiding the extractor and/or a guide wire into the cannulation of the implant.

Length of the threaded section of this embodiment may be about 2 cm, in some embodiments. In other embodiments, the length may be about 0.5 cm, 0.75 cm, 1 cm, 1.25 cm, 1.5 cm, 1.75 cm, 2.25 cm, 2.5 cm, 2.75 cm, or 3 cm. The diameter in this threaded portion may be about 7 mm, in some embodiments. In other embodiments, the diameter may be about 5 mm, 5.5 mm, 6 mm, 6.5 mm, 7.5 mm, 8 mm, 8.5 mm, or 9 mm. The threads may describe a forward thread, such that the thread is advanced with clockwise rotation or a reverse thread, whereby the threads advance with a counter-clockwise rotation of a matching male, externally threaded, device.

Figure 16A:
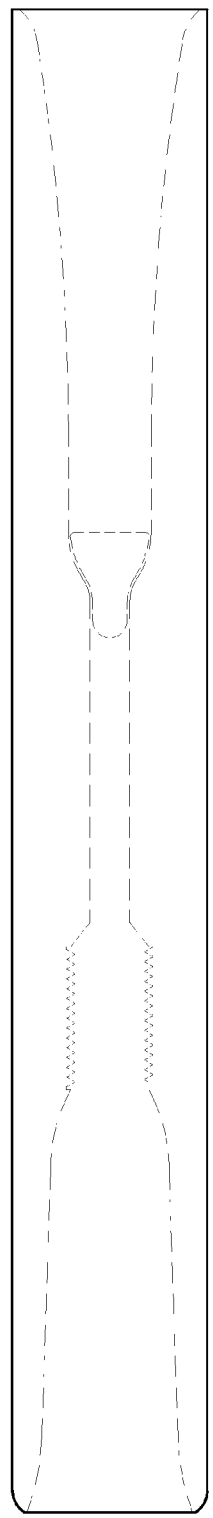
FIG. 16A is a view of an embodiment of a linkage device.
Figure 16B:
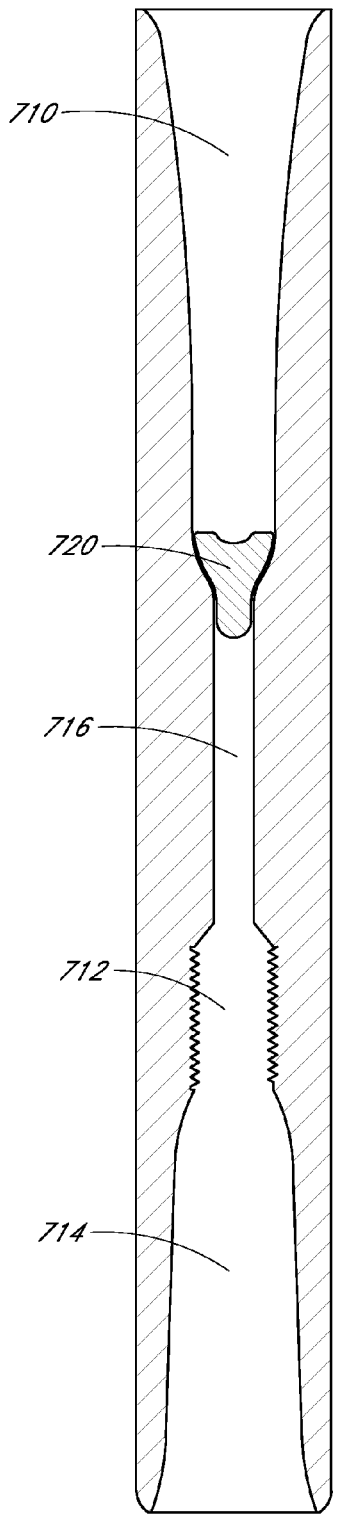
FIG. 16B is a longitudinal cross sectional view of the embodiment of FIG. 16A, with axial cross sections.

Now, turning attention to the distal, tapered portion of the linkage device 714, the taper may be configured to couple through a interference fit with the corresponding external taper of a distal femoral nail, as shown in FIGS. 16A-B. The length of this tapered section may be approximately 4 cm, in some embodiments. In other embodiments, the length may be about 2 cm, 2.5 cm, 3 cm, 3.5 cm, 4.5 cm, 5 cm, 5.5 cm, 6 cm, 6.5 cm, or 7 cm. After the transition 260 into the tapered section, there may be an increase in diameter of the opening to about 9 mm. In alternate versions, the diameter of the proximal edge of the tapered portion 234 may be about 7 mm, 8 mm, 10 mm, 11 mm, or 12 mm. The diameter gradually increases towards the distal end of the tapered section, with a final internal diameter at the distal end 254 of about 9 mm, 10 mm, 11 mm, 12 mm, 13 mm, 14 mm, 15 mm, 16 mm, 17 mm, or 18 mm. The length of the distal portion of the third distal section from the transition point 260 to the distal edge 254 may be about 4 cm. Alternatively, this segment may be about 2 cm, 2.5 cm, 3 cm, 3.5 cm, 4.5 cm, 5 cm, 5.5 cm, 6 cm, 6.5 cm, or 7 cm. As shown in FIGS. 16A-B, the proximal portion of the third, distal section may be threaded for use with an insertion tool, with the tapered portion 714 distally for frictional fit with the intramedullary fracture fixation device.

Inserter Tool and Complementary Intramedullary Nail

Figure 10:
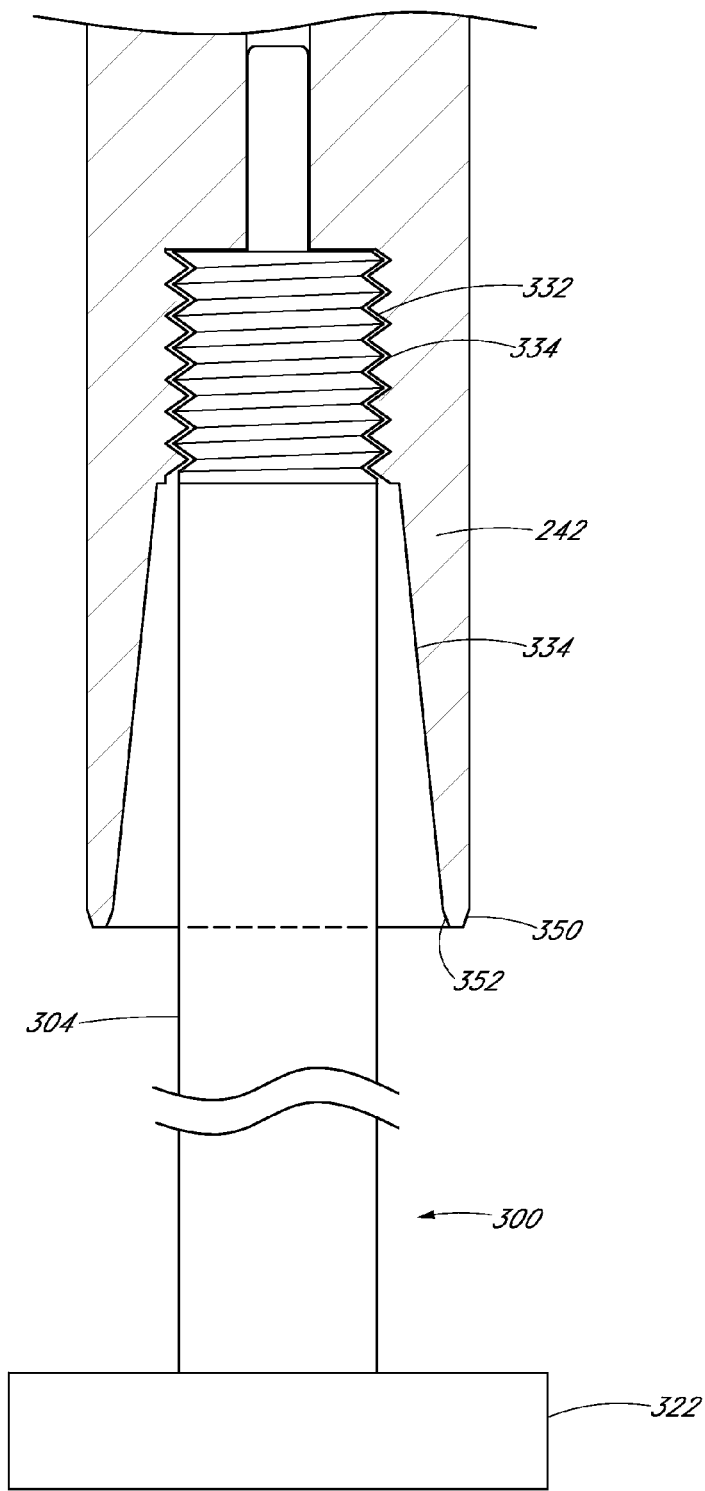
FIG. 10 is a view of the distal section of a femoral linkage implant coupled to the inserter.
Figure 11:
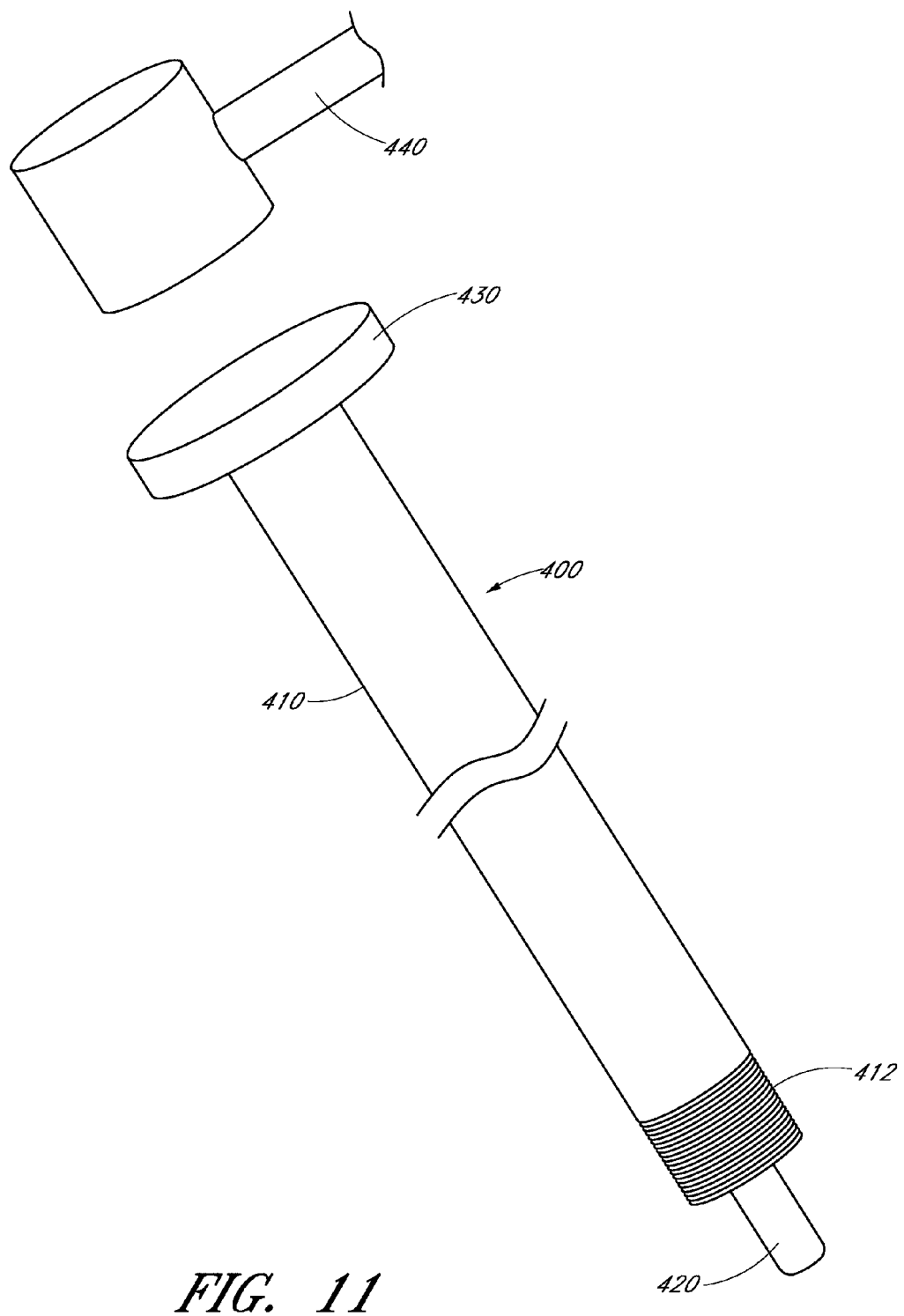
FIG. 11 is a view of an insertion guide.

Turning now to FIG. 10 of the distal segment 242 of the linkage device is shown coupled to an inserter tool 300. Coupling occurs between the internally threaded portion 332 of the linkage device and external threads on the male end of the inserter 324. In some embodiments, the inserter tool has a cylindrical extension 360 from the end of the threaded segment which corresponds to the diameter of the middle section 238 cannulation 226 of the linkage device 210. This may help center the inserter tool 300 before engaging the initial threads. The length of the extension may approximate the length of the central cannulation not occupied by a proximal plug or may occupy only a portion of the cannulation of the second section. The inserter tool may have a handle 322, a shaft 304 and a end coupling portion 324. The shaft may be straight and essentially cylindrical, or it may be curved or angled to ease insertion into the starting point at the knee. The inserter may either be threaded such that clockwise rotation advances the threads, or may be reverse-threaded such that rotation counter-clockwise advances the threads. The external diameter of the threaded end portion may be about 7 mm. The end-portion diameter may, alternatively, be about 5.5 mm, 6 mm, 6.5 mm, 7.5 mm, 8 mm, 8.5 mm, or 9 mm. The length of the threaded portion may match the length of the threaded portion of the linkage device. In addition to or as an alternate to the projection from the end of the tool may be a cannulation along the longitudinal length of the inserter tool from the handle to the tip. This may be sized to allow passage of a guidewire through the tool and into the cannulated portion of the linkage device 226. FIG. 11 demonstrates an embodiment of the insertion tool with a straight shaft 410, handle 430 with flat surface suitable for impaction with a mallet 440. Towards the end there is an externally threaded portion 412 and a projecting tip 420.

Figure 12:
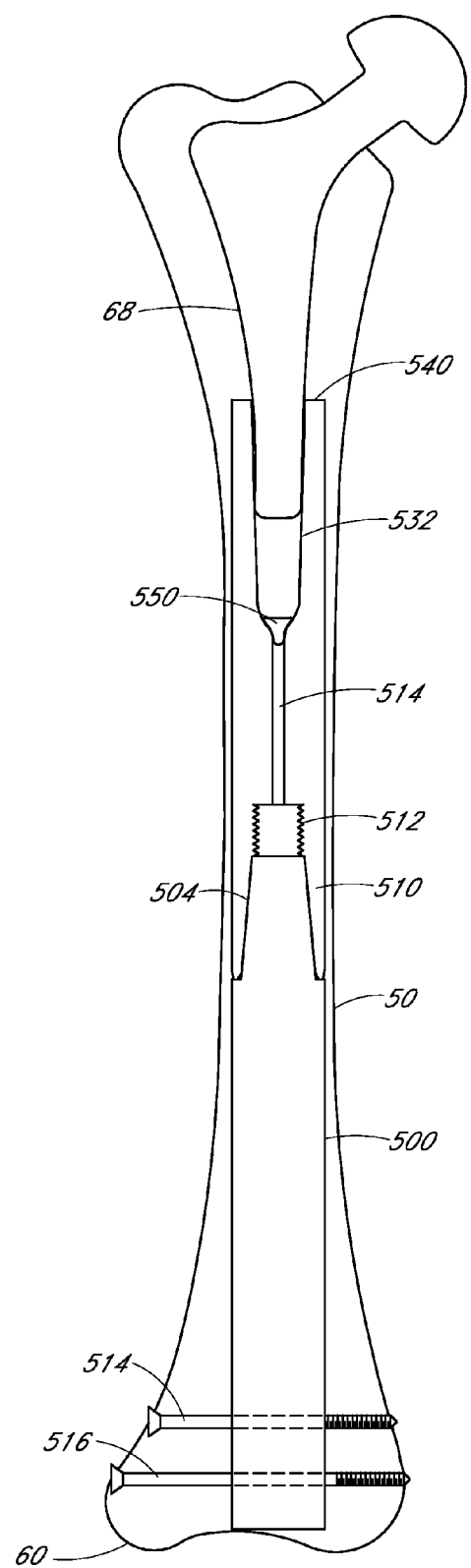
FIG. 12 is a view of the femur with hip prosthesis, linkage device, and distal femoral nail.

FIG. 12 shows a view of a femur with the linkage device and nail in position. The first, tapered section 532 and proximal end 540 can be seen intussuscepted over the preexisting intramedullary stem 68. In this embodiment, the frictional, interference fit between the prosthesis 68 and the linkage system occurs towards the proximal end of the linkage system 540. A plastic plug 550 sits at the junction between the first and the second segments of the nail. The second, cannulated segment 514 transitions into the threaded portion of the third, distal section of the linkage device 512. The nail is coupled with frictional, interference fit to the distal tapered portion 504 of the linkage device 510. The nail 500 extends from the knee to its fit with the linkage device and is seen to have cross screws 516, 514 to provide rotational stability.

Figure 13:
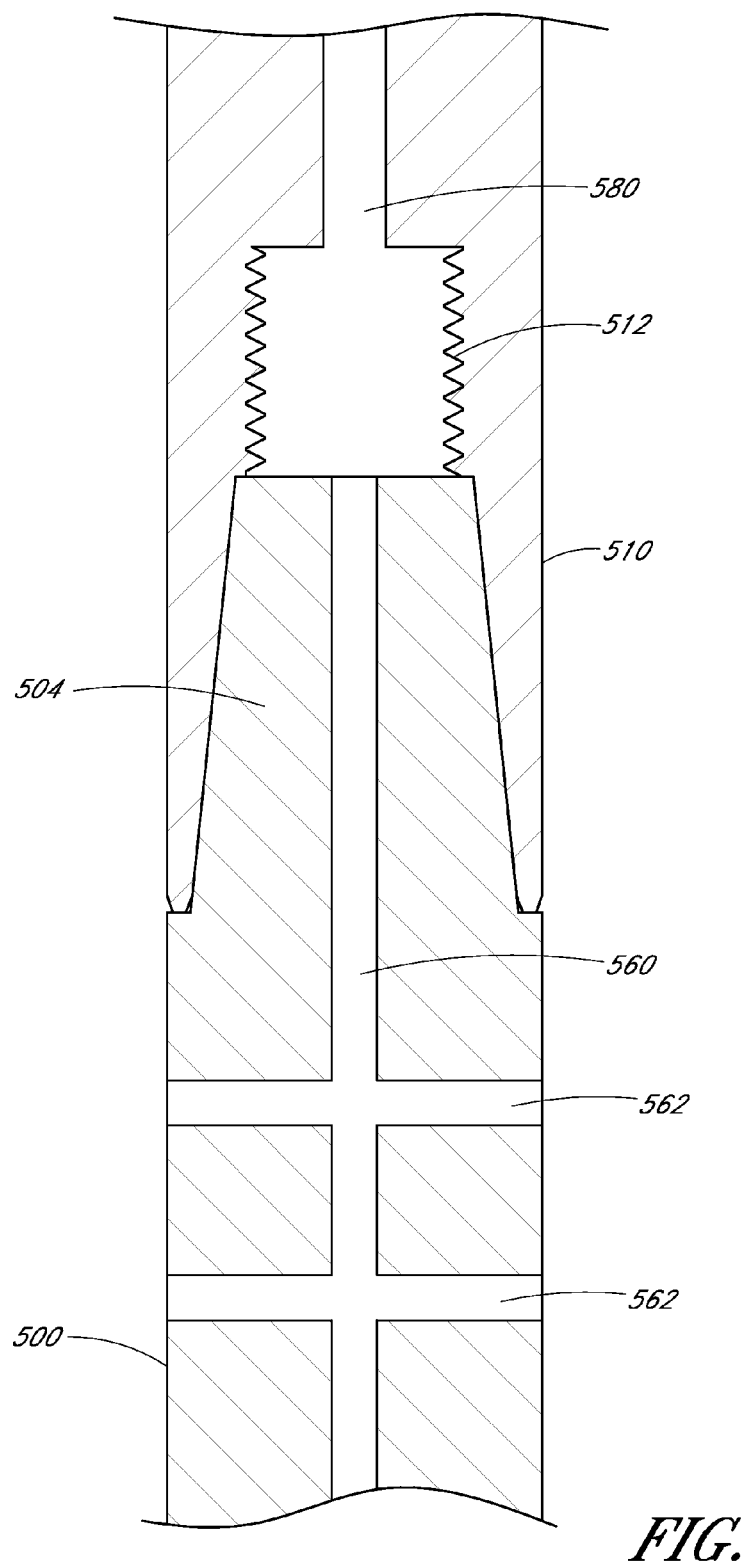
FIG. 13 is a close-up longitudinal cross-sectional view of the distal portion of a linkage device and proximal portion of a femoral nail.
Figure 14:
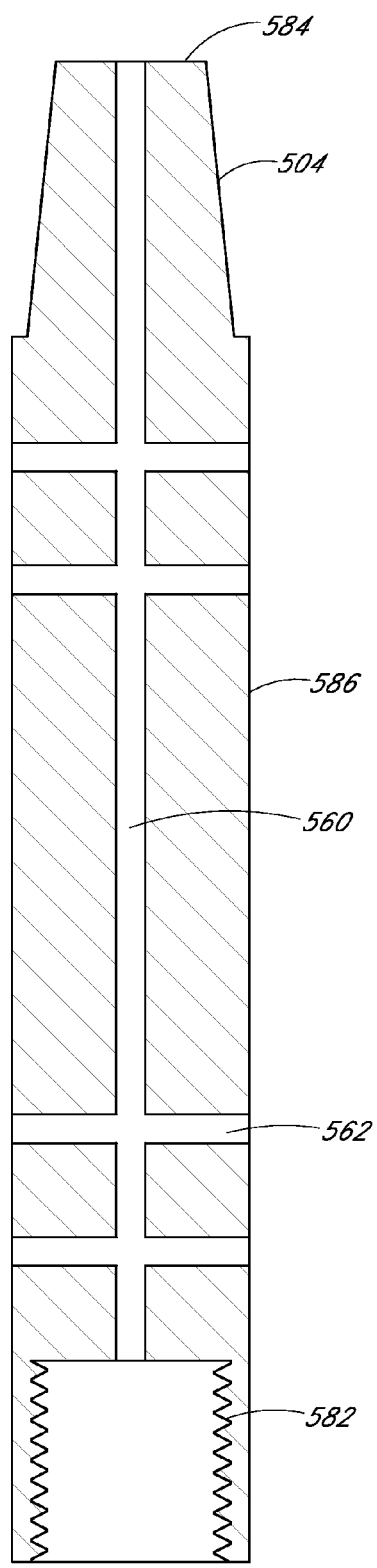
FIG. 14 is a view of a distal femoral nail.

In FIG. 13A, the threaded portion 512 and tapered portion 504 of the distal linkage device may be seen, as may be the frictional fit between the intramedullary retrograde femoral nail and the linkage device along the length of the tapered portion. Further features in embodiments of a retrograde femoral nail are a central cannulation 560 which allows passage of a guidewire and a transverse channels 562 adapted for a placement of a cross-screws. In FIG. 14, a retrograde femoral nail has a proximal end 584, central cannulation 560, channels for locking screws 562, a distal lumen 582 with internal threading for coupling with insertion and an extractor tools. Tapered area 504 is sized to provide an interference fit with the linkage device. The threaded portion distally 582 may have a diameter at and a threading congruent with those of the linkage device, such that the same inserter or extractor tool may be used for both.

Figure 15:
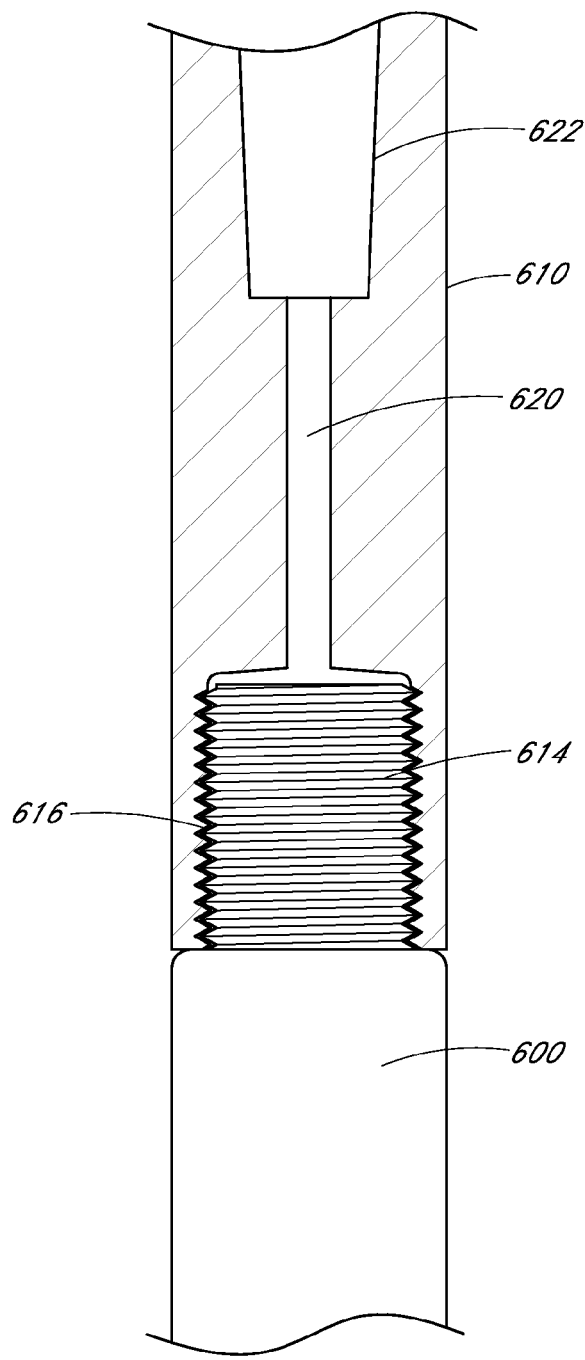
FIG. 15 is a view of an embodiment of the distal portion of a linkage device coupled to a distal femoral nail.

In FIG. 15, another arrangement of the distal, third section of the linkage device is shown. In this arrangement, the distal segment consists of a threaded, generally cylindrical area 616, which is configured to accept a threaded end 614 of either or both an inserter tool and a retrograde femoral nail 600. Either or both of these devices may have a projection from the end of the threaded portion which is sized to fit in the cannulated middle section 620 of the linkage device 610.

Other arrangements of the inserter tool and/or femoral nail will be obvious to one skilled in the art. For example, projections from the male end with corresponding indentations in the female receptor surface of the third section of the linkage device channel may be slidably engaged and control a rotation. In other embodiments of the linkage device, the distal end may have an extension of the cannulation 620, with a tapering of the external diameter towards the distal end of the linkage device. This may then engage with a complementary tapered channel at the proximal end of a distal femoral nail. In the alternative, this external diameter may be reduced at the distal end and have male threads for engagement with a corresponding female threaded channel in the proximal end of the femoral nail and/or the inserter/extractor tool.

A System for Implantation

The intramedullary linkage system also provides a kit for treatment of peri-prosthetic long-bone fractures. This includes a cylindrical linkage device with distal and proximal lumens configured to releasably couple with a first and a second intramedullary implant. The proximal channel is configured to reversibly couple with preexisting implants of varying shapes and sizes, such that it may be nearly universally coupled. The distal portion is configured to accept an end of an intramedullary device. A selection of intramedullary rods or nails are also provided, which are adapted to fit with the distal end of the linkage device, and are configured to be implanted in various bones and for various fracture types. Other tools may be provided, as well, including any combination or sub-combination of the following: inserter tool; extraction tool; locking screws for use with the intramedullary rod; guidewires; starting awl; end caps for the intramedullary rod; plugs for the proximal end of the linkage device; one or more reamers; a mallet; or a trephine. The trephine, if provided, may be configured such that it can be capable of cutting through a boney in-growth interface with a preexisting prosthetic stem, and/or removing cement. Also included may be a series of drill bits and/or taps.

The system may include multiple sizes of the linkage device. The device may come in a small, medium and large size, with differing external diameters. More or fewer sizes may be provided. The linkage devices and intramedullary implants may be provided in one or more metals, to match the preexisting implants. There will also be provided multiple sizes of the intramedullary nail, including multiple external diameters and a variety of lengths to fit the individual femur. A measuring guide may also be provided with the system. This measuring guide may fit within the distal portion of the linkage device, such that it measures from the junction 580 of the middle section and the distal section, or it may measure from the distal extent of the nail. An extraction tool may be provided as discussed above. This may have threads similar to the inserter, with a threading opposite to that of the insertion tool, or both a matching and opposing thread. A slideable mallet head along the shaft may assist in a device removal, or a mallet with a cut-out area to accommodate the shaft may be provided.

The system may be provided in a kit form. The kit may comprise instrumentation for use with the disclosed linkage device and/or intramedullary nails. The kit may further comprise a selection of linkage devices and/or intramedullary nails which are available for choice. In other kits, the linkage device/s and/or intramedullary nails may be provided pre-sterilized in individual packaging.

A Method for Use

There will now be described a method for use of the intramedullary linkage device. The method comprises the steps of identifying a patient with a preexisting intramedullary implant and a fracture of the same bone which now requires fixation. The intramedullary canal is accessed from the end of the long-bone opposite to the preexisting implant and the fracture is reduced. The intramedullary cavity is prepared and an appropriately sized linkage device is selected and impacted into position over the preexisting implant tip. An intramedullary nail is then chosen with appropriate diameter and length and this is removably coupled to the linkage device. Optionally, holes are drilled and locking screws are placed in one or more transverse screw channels through the intramedullary rod.

In some patients, after preparing the intramedullary channel, the linkage device may have a funnel-shaped plug placed at the base of the first section of the central channel, such that the cannulated area is blocked. In some embodiments, the intramedullary linkage device may be provided with an integrated plug, without central cannulation, or with a removable plug already in place. Prior to inserting the linkage device, polymethylmethacrylate (PMMA) or other bone cement is mixed in the usual manner and a quantity is placed into the proximal section of the linkage device. The linkage device is then impacted into the intramedullary canal until friction fit is accomplished between the tapered proximal section and the preexisting implant. Continued longitudinal force may be placed until the cement has cured by pushing on the handle of the inserter tool.

A method of extraction of the intramedullary nail and device is also provided. Extraction of intramedullary devices after they have been implanted for some time may be difficult. Aspects of the linkage device are advantageous to removal of the implants. For example, the intramedullary nail may be extracted by coupling it to an extraction tool, rotating it either in a clockwise or counter-clockwise direction, depending on whether the extraction tool is forward or reverse-threaded. After any locking screws are removed, in embodiments where coupling between the intramedullary and linkage device have been accomplished by interference fit, a mallet may be used to impact the under-surface of the extraction tool handle such that longitudinal force is applied away from the leading end of the implant, and the implant is removed. Alternatively, the extraction tool may have a built in slap hammer. An extraction tool is then coupled to the linkage device and it is also removed. In some embodiments, this may be accomplished using the same extraction tool as used for the intramedullary nail removal. A terminal tightening of the threads of the extraction tool into the threads of the insertion device may initiate disruption of the frictional interference fit of the device to the preexisting prosthesis. Torqueing, either in one direction or back-and-forth, of the coupled extraction tool and linkage device may also assist in initial loosening of the prosthesis-linkage fit. Impacting the tool handle longitudinally such that force is applied opposite to the direction of insertion will allow extraction and removal of the linkage device from the intramedullary canal. In embodiments where the coupling between the linkage device and the intramedullary nail occurs is accomplished by threading the nail tip into the linkage device, extraction may be accomplished in one step.

As discussed earlier, in instances where a plug is placed and cement used to enhance fixation and/or fit between the linkage device and the preexisting prosthetic implant, the removable plug can facilitate the extraction, by permitting dissociation of the cement plug from the linkage device from the interior wall of the linkage device via shear forces rather than in a direction perpendicular to the interface. The plug may be left in position or removed with the implant.

The inserter tool shaft may be rigid or have a degree of flexibility to accommodate the patient's anatomy. It may have a curve or be straight along the shaft. The shaft may have a narrowed diameter toward the end to fit more easily into the intramedullary canal during placement and extraction of the device. Inserter and extraction tools may be provided for the intramedullary rod which may also be used for the linkage device. Such dual-use tools may have extension components for use in placement or extraction of the linkage device, to accommodate the extra length required for insertion into the intramedullary canal.

While it may be preferred that the linkage device is inserted before the intramedullary rod is selected, so that measurement is taken with the device in situ; in some situations, both devices may, in some methods, be preselected and coupled prior to insertion into the intramedullary canal.

In situations where the fracture is severely comminuted, the native bone is particularly weak, there is a high risk of nonunion, or there is a need for a supplementary fixation, after placement of the linkage device and intramedullary nail, a supplementary side plate may be utilized. A supplemental plate of appropriate length, as determined by the surgeon, may be applied to the side of the affected bone, after surgical exposure through standard surgical approaches, and cable fixation used to couple the plate to the bone.

In cases where it is deemed appropriate, the surgeon may opt to utilize bone graft, growth factors, bone marrow aspirate, or other supplemental healing modalities. Bone graft options include autogenous, autologous, or synthetic cancellous bone graft or structural graft, such as cortical struts. These may be delivered to the site via incision, injection, or by application to the intramedullary device/s.

A trephine tool adapted specifically for use with the linkage device may also be provided. Multiple sizes of this trephine tool may be supplied, which may be sequentially placed in the intramedullary canal and used to provide exposure of the distal tip of the preexisting implant. These may be rotated and/or impacted to create a channel for the proximal end of the linkage device by disrupting any bony in-growth which would prevent intussusception of the linkage device over the tip of the implant to obtain an optimal friction, interference fit. Similarly, the trephines may function as broaches, creating a cavity in the shape of the proximal section of the selected linkage implant. The linkage implant may then be impacted into position against the prosthesis tip without encountering obstruction. The trephine may include a sharp leading edge. The trephine may be used with various methods of removing cement plugs for cemented prostheses. Alternatively, it may create a channel through the cement plug into which the linkage device may later be passed.

It is to be understood that the methods above are intended as exemplary rather than exclusive and that the order in which actions are performed may vary as may the particular actions, without departing from the disclosed method.

A Custom Implant

Although a limited number of linkage device implants will permit coupling with the vast majority of previously placed prostheses, there may be situations where the patient's anatomy and/or the preexisting intramedullary device prevent the standard sized linkage devices from accommodating them. In such situations, a custom implant may be made. Pre-operative radiographs, CT scans, or other imaging modalities may be obtained and used, along with any prior medical records, to provide measurements to determine the external diameter of the custom implant, length of the implant, and internal diameter measurements for the tapered portion proximally. The distal segment may comprise geometry specifically machined to couple with a surgeon's preferred intramedullary devices.

Additional Embodiments

While description of embodiments has been primarily directed toward femoral fractures in bones with preexisting hip nails or femoral hip prostheses, it is understood by one skilled in the art that the intramedullary linkage devices, intramedullary nail systems, and implantation methods could be used in other situations, wherein a long-bone has both a preexisting implant occupying part of its intramedullary cavity and a fracture either around the prosthesis or in another portion of the bone. For example, the linkage device may be used prophylactically in the setting of a preexisting hip or knee implant when a patient does not have a fracture, but desires replacement of the opposing joint, in which an intramedullary component is necessary. If there is concern regarding the native bone quality, a linkage device could be placed to join the two implants such that support for the bone is provided along the shaft length.

It is also understood that the linkage device may be used with an antegrade femoral nail or hip nail in a femur with a femoral component of a knee replacement that comprises an intramedullary stem. For this situation, a selection of nails with appropriate lengths and coupling features such as those described for a retrograde nail may be provided. Creation of a custom nail would also be an option in this situation. Also, additionally or alternatively, an embodiment of a linkage device may be provided in which both the first and third segments of the channel are tapered to permit a universal friction fit coupling. This would allow the linkage device to capture the intramedullary stem of the knee implant while also accommodating an antegrade femoral nail or hip nail from a standard array of implants.

Other applications in which the linkage device and/or system could be used include humeral fractures around either an elbow replacement or partial or a total shoulder replacement are preexisting, or fractures of the tibia, the forearm, or other long-bones with devices occupying part of the intramedullary canal. For these applications, it is understood by one skilled in the art to manufacture linkage devices with dimensions appropriate for the intramedullary canal of the bone and typical intramedullary devices.

Although this invention has been disclosed in the context of certain preferred embodiments and examples, it will be understood by those skilled in the art that the present invention extends beyond the specifically disclosed embodiments to other alternative embodiments and/or uses of the invention, and obvious modifications and equivalents thereof. Additionally, it is contemplated that various aspects and features of the invention described can be practiced separately, combined together, or substituted for one another, and that a variety of combinations and sub-combinations of the features and aspects can be made and still fall within the scope of the invention. Further, the disclosure herein of any particular feature, aspect, method, property, characteristic, quality, attribute, element or the like in connection with an embodiment can be used in all other embodiments set forth herein. Thus, it is intended that the scope of the present invention disclosed should not be limited by the particular disclosed embodiments described above, but should be determined only by a fair reading of the claims.

Conditional language, such as, among others, "may," "could," "might" or "may," unless specifically stated otherwise, or otherwise understood within the context as used, is generally intended to convey that certain embodiments include, while other embodiments do not include, certain features or elements. Thus, such conditional language is not generally intended to imply that features or elements are in any way required for one or more embodiments.

What is claimed is:

1. A fracture repair system for use with a pre-existing implanted hip prosthesis previously implanted in a patient's intramedullary canal of the femur, the system comprising:
   a linkage device, comprising:
      an elongate, rigid body having a first end and a second end, wherein the proximal surface of the first end is configured for leading edge implantation of the linkage device and having a sharpened edge for cutting bone;
      a substantially smooth outer surface; and
      a lumen extending through the elongate body from the first end to the second end, the lumen comprising:
         a first proximal section adjacent the first end, having a smooth non-threaded inner diameter sized to mate in a friction fit with a distal portion of the pre-existing hip prosthesis, wherein the inner diameter of the first section tapers inwardly from the first end toward the second end to form a wide mouth at the first end configured to receive hip prostheses of varying cross-sectional dimensions;
         a second distal section adjacent the second end, wherein at least a portion of the second section is internally threaded and configured to removably receive an insertion tool for distal to proximal insertion of the linkage device into the femur; and
         a central section disposed between the first and second sections and having an inner diameter smaller than either the first section inner diameter or the second section inner diameter; and
   an intramedullary fracture fixation device co-axially and linearly aligned along its entire length with the linkage device, the fixation device comprising a proximal leading end and a distal trailing end, the leading end being externally threaded for removable coupling to the internally threaded second section of the linkage device lumen and having the same diameter and interchangeable with the insertion tool.

2. The linkage device for use in the intramedullary canal of a long bone of claim 1, wherein the first end of the elongate, rigid body is beveled.

3. The linkage device for use in the intramedullary canal of a long bone of claim 1, wherein the first section of the lumen is tapered such that an angle between an outer wall of the first section and the inner wall of the first section is between 0.5 and 10 degrees.

4. The linkage device for use in the intramedullary canal of a long bone of claim 3 wherein the angle between the outer wall and inner wall of the first section is constant.

5. The linkage device for use in the intramedullary canal of the long bone of claim 4 wherein the angle between the outer wall and inner wall of the first section increases from the first end of the linkage device toward the second end.

6. The linkage device for use in the intramedullary canal of a long bone of claim 1 further comprising a plug in the distal portion of the first section of the linkage device which extends into the lumen of the central section of the linkage device.

7. The linkage device for use in the intramedullary canal of a long bone of claim 1 wherein the lumen of the second section comprises a tapered portion adjacent the second end of the linkage device and a threaded portion adjacent the central portion of the linkage device.

8. The linkage device for use in the intramedullary canal of a long bone of claim 7 wherein the threaded portion is configured to mate with an inserter tool.

9. The linkage device for use in the intramedullary canal of a long bone of claim 7 wherein the tapered portion is configured to mate with the intramedullary portion of the second implant.

10. The linkage device for use in the intramedullary canal of a long bone of claim 1, wherein the first section is between 3 and 6 cm. in length, the second section is between 3 and 6 cm in length and the central section is between 1 and 4 cm in length.

11. The linkage device for use in the intramedullary canal of a long bone of claim 1, wherein the external diameter of the linkage device is between 9 and 16 mm.

12. A method for peri-prosthetic long bone fracture fixation, comprising:
    preparing an intramedullary canal of a fractured long bone with a preexisting hip prosthesis stem;
    inserting an intramedullary linkage device into the intramedullary canal in a distal to proximal direction wherein the intramedullary linkage device comprises an elongate body with a first end and a second end with a lumen extending through the elongate body from the first end to the second end wherein the lumen comprises a first section adjacent the first end wherein a wall of the lumen describes a taper wherein a widest diameter of the lumen in the first section is adjacent the first end, and a second section adjacent the second end wherein the lumen is configured to accommodate an intramedullary fracture fixation device;
    obtaining a friction fit between the first section of the intramedullary linkage device and the preexisting hip prosthesis stem;
    inserting in a distal to proximal direction an intramedullary fracture fixation device into the intramedullary canal; and
    coupling the intramedullary fracture fixation device to the second section of the intramedullary linkage device.

13. The method for peri-prosthetic long bone fracture fixation of claim 12, wherein coupling the intramedullary fracture fixation device to the second section of the intramedullary linkage device comprising obtaining a friction fit between the second section of the intramedullary linkage device and the intramedullary fracture fixation device.

14. The method for peri-prosthetic long bone fracture fixation of claim 12 further comprising coupling an inserter tool to the second section of the intramedullary linkage device prior to inserting the intramedullary linkage device in the intramedullary canal.

15. A system for peri-prosthetic long bone fracture fixation, the system for use with a pre-existing implanted hip prosthesis previously implanted into a patient's intramedullary canal of the femur, comprising:
 an at least one intramedullary linkage device, comprising:
  an elongate body with a first end and a second end, the first end being proximal to the second end and being configured for cutting bony ingrowth; and
  a lumen extending through the elongate body from the first end to the second end wherein the lumen comprises:
   a first section adjacent the first end wherein a wall of the lumen describes a taper wherein a widest diameter of the lumen in the first section is adjacent the first end and is sized to mate with the distal portion of the pre-existing implanted hip prosthesis, and
   a second section adjacent the distal second end, at least a portion of the second section is internally threaded and configured to removably receive an insertion tool for distal to proximal insertion of the linkage device in the femur; and
   a central section disposed between the first and second sections; and
 at least one intramedullary fracture fixation device configured for substantial co-axial and linear alignment along its entire length with the linkage device, the fixation device comprising a proximal leading end and a distal trailing end wherein the leading end is configured to co-axially and removably couple with the distal second section of the intramedullary linkage device.

16. The system for peri-prosthetic long bone fracture fixation of claim 15 further comprising an inserter tool.

17. The system for peri-prosthetic long bone fracture fixation of claim 15 further comprising a trephine.

18. The system for peri-prosthetic long bone fracture fixation of claim 15 comprising two or more intramedullary linkage devices in which an external diameter of one intramedullary linkage device is smaller than an external diameter of the second intramedullary linkage device.

* * * * *